(12) United States Patent
Hatcher, Jr. et al.

(10) Patent No.: US 9,154,743 B2
(45) Date of Patent: *Oct. 6, 2015

(54) SYSTEM AND METHOD FOR OPTICAL INSPECTION OF OFF-LINE INDUSTRIAL GAS TURBINES AND OTHER POWER GENERATION MACHINERY WHILE IN TURNING GEAR MODE

(71) Applicant: Siemens Energy, Inc., Orlando, FL (US)

(72) Inventors: Clifford Hatcher, Jr., Orlando, FL (US); Richard Hatley, Morristown, NJ (US)

(73) Assignee: Siemens Energy, Inc., Orlando, FL (US)

( * ) Notice: Subject to any disclaimer, the term of this patent is extended or adjusted under 35 U.S.C. 154(b) by 9 days.

This patent is subject to a terminal disclaimer.

(21) Appl. No.: 13/971,938

(22) Filed: Aug. 21, 2013

(65) Prior Publication Data

US 2013/0335549 A1 Dec. 19, 2013

Related U.S. Application Data

(63) Continuation-in-part of application No. 13/362,352, filed on Jan. 31, 2012, now Pat. No. 8,713,999, and a continuation-in-part of application No. 13/362,417, filed on Jan. 31, 2012, and a continuation-in-part of (Continued)

(51) Int. Cl.
*G01M 15/14* (2006.01)
*H04N 7/18* (2006.01)
(Continued)

(52) U.S. Cl.
CPC ............... *H04N 7/18* (2013.01); *F01D 21/003* (2013.01); *G01N 21/954* (2013.01); *G02B 23/2484* (2013.01)

(58) Field of Classification Search
CPC ........................................................ G01M 15/14
USPC ................ 73/112.01, 112.03, 112.05, 118.03
See application file for complete search history.

(56) References Cited

U.S. PATENT DOCUMENTS 5,102,221 A 4/1992 Desgranges et al.
5,164,826 A 11/1992 Dailey (Continued)

FOREIGN PATENT DOCUMENTS

EP 0907077 4/1999

OTHER PUBLICATIONS

Co-pending U.S. Appl. No. 13/362,417, filed Jan. 31, 2012.

(Continued)

*Primary Examiner* — Eric S McCall

(57) ABSTRACT

Internal components of gas and steam turbines are inspected with an optical camera inspection system that is capable of automatically and/or manually positioning the camera field of view (FOV) to an area of interest within the turbine along a pre-designated navigation path and capturing images with or without human intervention. Camera positioning and image capture can be initiated automatically or after receipt of operator permission. The inspection system includes an articulated multi-axis inspection scope with an optical camera that is inserted through a combustor nozzle access port, combustor and transition, so that the camera FOV captures the leading edge of Row 1 rotating turbine blades while the rotor is spinning at up to 1000 RPM. An illumination system strobe light and the camera image capture are synchronized with the blade rotation speed so that images of multiple or all blades may be obtained from a single inspection scope insertion point.

18 Claims, 19 Drawing Sheets

Related U.S. Application Data application No. 13/362,387, filed on Jan. 31, 2012, now Pat. No. 8,922,640.

(60) Provisional application No. 61/692,409, filed on Aug. 23, 2012, provisional application No. 61/692,393, filed on Aug. 23, 2012.

(51) Int. Cl.
*F01D 21/00* (2006.01)
*G01N 21/954* (2006.01)
*G02B 23/24* (2006.01)

(56) References Cited

U.S. PATENT DOCUMENTS

| | | | |
|---|---|---|---|
| 5,349,850 A * | 9/1994 | Young | 73/112.01 |
| 6,317,387 B1 | 11/2001 | D'Amaddio | |
| 6,992,315 B2 * | 1/2006 | Twerdochlib | 250/559.08 |
| 7,068,029 B2 * | 6/2006 | Hatcher et al. | 324/239 |
| 7,271,894 B2 | 9/2007 | Devitt et al. | |
| 7,489,811 B2 * | 2/2009 | Brummel et al. | 382/152 |
| 7,956,326 B1 | 6/2011 | Kychakoff et al. | |
| 8,184,151 B2 * | 5/2012 | Zombo et al. | 348/82 |
| 8,299,785 B2 | 10/2012 | Bousquet et al. | |
| 2004/0051525 A1 * | 3/2004 | Hatcher et al. | 324/262 |
| 2004/0193016 A1 | 9/2004 | Root | |
| 2005/0199832 A1 * | 9/2005 | Twerdochlib | 250/559.29 |
| 2005/0200355 A1 * | 9/2005 | Hatcher et al. | 324/239 |
| 2006/0088793 A1 * | 4/2006 | Brummel et al. | 431/13 |
| 2007/0129604 A1 * | 6/2007 | Hatcher et al. | 600/136 |
| 2007/0157733 A1 * | 7/2007 | Litzenberg et al. | 73/644 |
| 2007/0296964 A1 | 12/2007 | Nishimura et al. | |
| 2011/0018530 A1 | 1/2011 | Bousquet et al. | |
| 2011/0267428 A1 | 11/2011 | George et al. | |
| 2012/0154594 A1 | 6/2012 | Xie et al. | |
| 2012/0281084 A1 * | 11/2012 | Hatcher et al. | 348/83 |
| 2013/0194412 A1 * | 8/2013 | Hatcher et al. | 348/82 |
| 2013/0194413 A1 * | 8/2013 | Hatcher et al. | 348/82 |
| 2014/0168420 A1 | 6/2014 | Naderhirn | |

OTHER PUBLICATIONS

Co-pending U.S. Appl. No. 13/972,200, filed Aug. 21, 2013.

\* cited by examiner

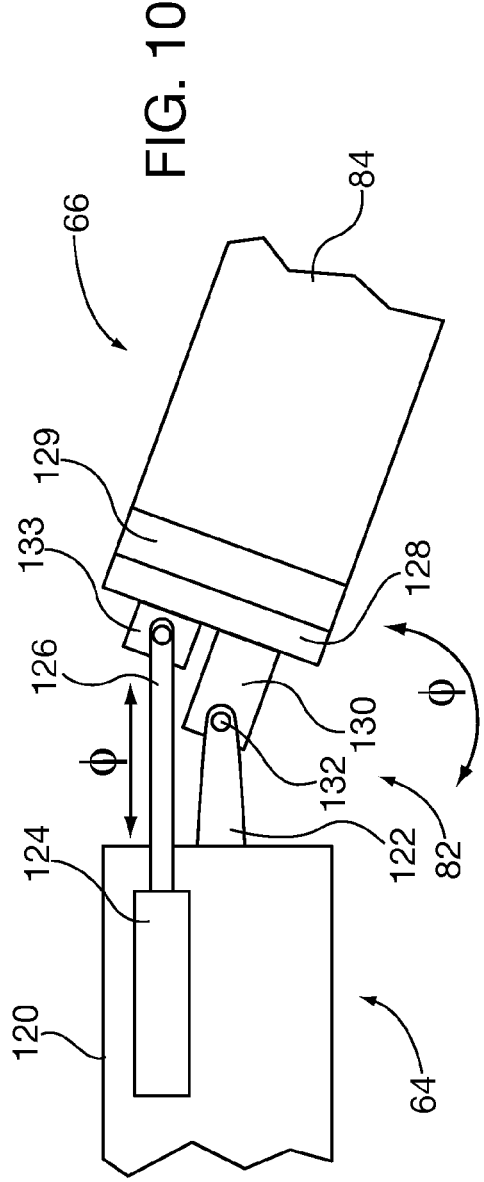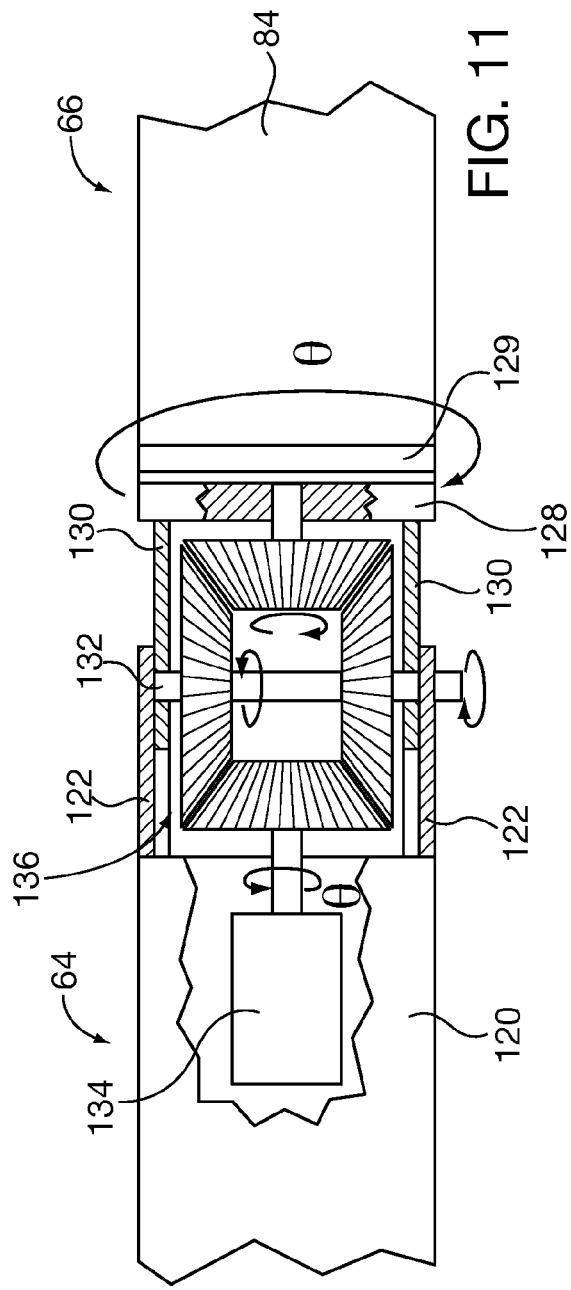

US 9,154,743 B2

SYSTEM AND METHOD FOR OPTICAL INSPECTION OF OFF-LINE INDUSTRIAL GAS TURBINES AND OTHER POWER GENERATION MACHINERY WHILE IN TURNING GEAR MODE

REFERENCE TO CO-PENDING APPLICATIONS

This application is a continuation-in-part of United States utility patent application entitled "System And Method For Automated Optical Inspection Of Industrial Gas Turbines And Other Power Generation Machinery With Multi-Axis Inspection Scope", filed Jan. 31, 2012 and assigned Ser. No. 13/362,352, now U.S. Pat. No. 8,713,999.

This application claims the benefit of United States provisional patent application entitled "Hybrid Scope—Turbine Combustor Hardware Visual Inspection Tooling That Can Also Be Used To Inspect The Row 1 Turbine Blades While They Are On Turning Gear (1-1000 rpm)" filed Aug. 23, 2012 and assigned Ser. No. 61/692,393, which is incorporated by reference herein.

This application also claims the benefit of the following co-pending United States applications: United States utility patent application entitled "System And Method For Automated Optical Inspection Of Industrial Gas Turbines And Other Power Generation Machinery, filed Jan. 31, 2012 and assigned Ser. No. 13/362,417; United States utility patent application entitled "System And Method For Automated Optical Inspection Of Industrial Gas Turbines And Other Power Generation Machinery With Multi-Axis Inspection Scope", filed Jan. 31, 2012 and assigned Ser. No. 13/362,387, now U.S. Pat. No. 8,922,640; and co-pending United States utility patent application entitled "System And Method For Visual Inspection And 3D White Light Scanning Of Off-Line Industrial Gas Turbines And Other Power Generation Machinery", filed concurrently herewith, and assigned Ser. No. 13/972,000 that in turn claims the benefit of United States provisional patent application entitled "Vision Scope—3D Scanner Tip for Visual Inspection and Measurement" filed Aug. 23, 2012 and assigned Ser. No. 61/692,409. All of said cited co-pending cited applications are incorporated by reference herein.

BACKGROUND OF THE DISCLOSURE

1. Field of the Invention

The invention relates to optical camera systems for nondestructive internal inspection of industrial gas turbines and other power generation machinery, including by way of non-limiting example steam turbines and generators. More particularly, aspects of the invention relate to an optical camera inspection system that is capable of positioning the camera field of view (FOV) through a gas turbine combustor and transition and capturing images of Row 1 rotating turbine blades while the turbine engine is in turning gear mode, with or without human intervention. In some embodiments, camera positioning and image capture can be initiated automatically or after receipt of operator permission. In other embodiments camera positioning can be performed manually.

2. Description of the Prior Art

Power generation machinery, such as steam or gas turbines, are often operated continuously with scheduled inspection and maintenance periods, at which time the turbine is taken off line and shut down. By way of example, a gas turbine engine often will be operated to generate power continuously for approximately 4000 hours, thereupon it is taken off line for routine maintenance, inspection, and repair of any components identified during inspection. Taking a gas turbine off line and eventually shutting it down completely for scheduled maintenance is a multi-day project. Some turbine components, such as the turbine rotor section, are operated at temperatures exceeding 1000° C. (1832° F.). The turbine requires 48-72 hours of cooling time to achieve ambient temperature before complete shutdown in order to reduce likelihood of component warping or other deformation. During the shutdown phase the turbine rotor rotational speed is spooled down from operating speed of approximately 3600 RPM to a speed of approximately 120 RPM or less in "turning gear mode", where the rotor is externally driven by an auxiliary drive motor, in order to reduce likelihood of rotor warping. Other turbine components, such as the turbine housing, are also cooled slowly to ambient temperature.

Once the turbine is cooled to ambient temperature over the course of up to approximately 72 hours internal components of the now static turbine can be inspected with known optical camera inspection systems. Known optical camera inspection systems employ rigid or flexible optical bore scopes that are inserted into inspection ports located about the turbine periphery. The bore scope is manually positioned so that its field of view encompasses an area of interest within the turbine, such as one or more vanes or blades, combustor baskets, etc. A camera optically coupled to the bore scope captures images of objects of interest within the field of view for remote visualization and archiving (if desired) by an inspector.

If a series of different images of different areas of interest within a given turbine inspection port are desired, the operator must manually re-position the camera inspection system bore scope to achieve the desired relative alignment of internal area of interest and the field of view. Relative alignment can be achieved by physically moving the bore scope so that its viewing port is positioned proximal a static area of interest. Examples of such relative movement of bore scope and static turbine component are by inserting a bore scope in different orientations within a static combustor or radially in and out of space between a vane and blade row within the turbine section. Relative alignment can also be achieved by maintaining the bore scope viewing port in a static position and moving the turbine internal component of interest into the static viewing field. An example of relative movement of turbine internal component and static bore scope is inspection of different blades within a blade row by manually rotating the turbine rotor sequentially a few degrees and capturing the image of a blade. The rotor is rotated sequentially to align each desired individual blade in the row within the camera viewing field.

Complete turbine inspection requires multiple manual relative repositioning sequences between the camera inspection system viewing port and areas of interest within the turbine by a human inspector. Inspection quality and productivity is subject to the inspection and manipulation skills of the inspector and inspection team. Inspection apparatus positioning is challenging due to the complex manipulation paths between components in a gas turbine. For example, insertion of a bore scope through a combustor inspection port in order to inspect the leading edge of first row vanes or related supports requires compound manipulations Improper positioning of inspection apparatus within a turbine potentially can damage turbine internal components. Often an inspection team of multiple operators is needed to perform a manual inspection using known inspection methods and apparatus. In summary, known manual camera inspection procedures and inspection system manipulation are time consuming, repetitive in nature, and often require assistance of an inspection team of multiple personnel. The "human factor" required for known manual camera inspection procedures and inspection system manipulation introduces undesirable inspection process variances based on human skill level differences. Given human skill variances, some inspection teams are capable of completing inspections in less time, achieve better image quality and have lower inspection damage risk than other teams. Ideally skills of a high performing inspection team could be captured for use by all teams.

It is desirable to obtain inspection images of the leading edges of Row 1 blades in either gas or steam turbines, as they are often the most susceptible to operational thermal and/or mechanical damage. If images of the Row 1 blade leading edges can be obtained early and easily in the earliest possible stages of the cool down cycle—for example while the rotor is spinning at under 1000 RPM before the long turning gear mode part of the cool down cycle—blades needing repair can be prioritized for replacement, refurbishment and/or other repair days before the turbine rotor comes to a complete rest. Known bore scope inspection systems experience optical quality degradation within the fiber optic scope between the scope field of view (FOV) and the camera's objective lens and maintain constant illumination during an inspection procedure. These known bore scope physical constraints effectively limit their usefulness to obtaining images of static components; in other words when the rotor is at a complete stop. Otherwise the scope camera captures blurred images of the rotating blades.

A need exists in the art for optical camera inspection systems and methods that enable visual inspection of all Row 1 blades from a single, easily accessed inspection point while the turbine rotor is rotating at up to 1000 RPM.

An additional need exists in the art for optical camera inspection systems and methods that reduce total time necessary to perform a nondestructive internal inspection of power generation machinery, including by way of non-limiting example steam or gas turbines and generators than is attainable by known inspection apparatus and methods, so that the machinery can be brought back on line for resuming power generation more quickly during maintenance cycles.

Another need exists in the art for optical camera inspection systems and methods that are capable of positioning inspection apparatus within power generation machinery, including by way of non-limiting example steam or gas turbines and generators, consistently and repetitively within an individual machine's inspection cycle or within inspection cycles of multiple different machines, with minimized risk of damage to machine internal components, high image quality and quicker inspection cycling time than is attained by the known manual inspection apparatus and methods.

Yet another need exists in the art for optical camera inspection systems and methods that help to equalize inspection skill level and productivity among different inspection teams.

SUMMARY OF THE INVENTION

Accordingly, potential objects of the present invention, jointly or severally among others, are to create optical camera inspection systems and methods for power generation machinery, (including by way of non-limiting example steam or gas turbines and generators) that compared to known inspection apparatus and methods: reduce total scheduled maintenance period time and individual inspection cycle time; position inspection apparatus consistently and repetitively within an individual machine's inspection cycle or within inspection cycles of multiple different machines, with minimized risk of damage to machine internal components and high image quality; and that help to equalize inspection skill level and productivity among different inspection teams.

Another object of the optical inspection system of the present invention is to enable visual inspection of all Row 1 blades from a single, easily accessed inspection point while the turbine rotor is rotating at up to 1000 RPM.

These and other objects are achieved in accordance with the present invention by a system for internal inspection of a gas or steam turbine. The system includes a base for affixation to a turbine inspection port. The system also includes an inspection scope having an extendable elongated body defining a central axis, with a proximal end rotatively coupled to the base and a distal end for insertion within a turbine inspection port. The inspection scope has an extension portion intermediate the proximal and distal ends; and an articulation joint, having opposed first and second joint ends, with the first joint end coupled to the inspection scope distal end. A camera head, having a field of view, is coupled to articulation joint second joint end. A gross rotation drive is coupled to the inspection scope for rotating the inspection scope about its central axis. A scope extension drive is coupled to the extension portion for translating the extension. An articulation drive is coupled to the camera head, for articulating the camera head field of view relative to the inspection scope central axis. A camera is coupled to the camera head, for capturing an image within the field of view. An illumination system selectively illuminates the camera field of view. The system also has a control system, coupled to the gross rotation, scope extension and articulation drives the camera and the illumination system, for positioning the inspection scope and field of view along a navigation path within a turbine to an internal area of interest, as well as for selectively illuminating the camera field of view with the illumination system and capturing camera images at rates corresponding to a turbine rotor rotational speed. In some embodiments the illumination system operates in a first mode to illuminate the camera field of view constantly, such as when imaging Row 1 stationary vanes, and switches to a strobe lighting second mode to capture images of Row 1 turbine blades as the off-line turbine rotor rotates.

In embodiments of the present invention the inspection scope the base is affixed to an off-line gas turbine combustion section, with the inspection scope being inserted through a combustor pilot nozzle port, through the transition, with the camera field of view oriented to capture images of Row 1 vanes and blades. The illumination system is pulsed at a strobe rate corresponding to the rotor RPM so that images of a plurality of the rotating blades can be captured from a single inspection scope insertion point.

The present invention also features a system for internal inspection of a steam or gas turbine, including a base for affixation to a gas turbine inspection port. The system also includes an inspection scope having an extendable elongated body defining a central axis, with a proximal end rotatively coupled to the base and a distal end for insertion within a turbine inspection port. An extension portion is intermediate the proximal and distal ends. The inspection scope has an articulation joint, having opposed first and second joint ends, with the first joint end coupled inspection scope distal end. A camera head extension is coupled to the articulation joint second end. This extension has a camera head telescoping portion as well as a camera head rotation/pan joint that is also coupled to the articulation joint second end. The inspection scope has a camera head, having a field of view, coupled to the camera head extension and the camera head rotation/pan joint. The inspection scope has drives for motion axes. A gross rotation drive rotates the inspection scope about its central axis. A scope extension drive translates the extension portion, and an articulation drive articulates the camera head field of view relative to the inspection scope central axis. A camera head extension drive translates the camera head telescoping portion, and a camera head rotation/pan drive rotates the camera head. A camera is coupled to the camera head, for capturing an image within the scope field of view. The inspection system has an illumination system for selectively illuminating the camera field of view. A control system is coupled to the respective gross rotation, scope extension, articulation, camera head extension and camera head rotation/pan drives and the camera, for positioning the inspection scope and field of view along a navigation path within a turbine to an internal area of interest, as well as for selectively illuminating the camera field of view with the illumination system and capturing camera images at rates corresponding to a turbine rotor rotational speed. In some embodiments the camera is a global shutter or full frame camera that captures all camera pixel images approximately simultaneously and the captured images are of Row 1 blades.

The present invention also features a method for internal inspection of a steam or gas turbine, and includes the step of providing an internal inspection system. The inspection system has a base for affixation to a turbine inspection port and an inspection scope coupled to the base. More particularly, the inspection scope has an extendable elongated body defining a central axis, with a proximal end rotatively coupled to the base and a distal end for insertion within a turbine inspection port. The inspection scope has an extension portion intermediate the proximal and distal ends; and an articulation joint, having opposed first and second joint ends, with the first joint end coupled to the inspection scope distal end. A camera head, having a field of view, is coupled to articulation joint second joint end. The inspection scope also has multiple drives for imparting selective motion to the scope. A gross rotation drive rotates the inspection scope about its central axis. A scope extension drive translates the extension portion. An articulation drive articulates the camera head field of view relative to the inspection scope central axis. A camera is coupled to the camera head, for capturing an image within the inspection scope field of view. The system includes a control system, coupled to the gross rotation, scope extension and articulation drives and the camera, for positioning the inspection scope and field of view along a navigation path within a turbine to an internal area of interest and for capturing a camera image thereof. The inspection scope so provided also has an illumination system for selectively illuminating the camera field of view that is coupled to the control system. The inspection method is further performed by rotating an off-line turbine rotor at a rotational speed and affixing the base to a turbine inspection port, such as a combustor nozzle port. The turbine is inspected by positioning the inspection scope and camera head field of view along a navigation path with the control system. The illumination system selectively illuminates the camera field of view at strobe rates corresponding to the turbine rotor rotational speed. Camera images are captured at rates corresponding to the turbine rotor rotational speed. In some embodiments the camera is a global shutter or full frame camera that captures all camera pixel images approximately simultaneously and the captured images are of Row 1 blades.

Advantageously, the navigation path may be pre-determined by a number of methods and subsequently recorded for future replication by the control system of the actual inspection scope used in the inspecting step. The navigation path pre-determination methods may include: prior human controlled positioning of an inspection scope of the type used in the inspecting step within the actual inspected gas turbine (or within another gas turbine having the same type of internal structure as the actual inspected gas turbine) along a selected navigation path; human controlled simulated positioning of a virtual inspection scope of the type used in the inspecting step within a virtual power generation machine of the type being inspected along a selected navigation path; and simulated positioning of a virtual inspection scope and virtual power generation machine of the type used in the inspecting step along a simulated selected navigation path without human intervention.

In other embodiments practicing the methods of the present invention, the provided inspection system is used for capturing images of a gas turbine Row 1 vanes and Row 1 blades components, comprising coupling the base to a gas turbine combustor pilot nozzle port; inserting the inspection scope through a gas turbine combustor pilot nozzle port; and illuminating the camera field of view while navigating the camera along a navigation path through the combustor and an adjoining combustor transition upstream of Row 1 blades and vanes components independent of turbine rotor rotational speed. A first camera image of at least one of the Row 1 vane components is captured with the provided inspection system articulation joint in a first position. The camera field of view is selectively illuminated with the illumination system at strobe rates corresponding to the turbine rotor rotational speed. The articulation joint is articulated to a second position, so that the camera captures respective second camera images of plural rotating Row 1 blade components. In some embodiments the camera is a global shutter or full frame camera that captures all camera pixel images approximately simultaneously and the captured images are of Row 1 blades.

The objects and features of the present invention may be applied jointly or severally in any combination or sub-combination by those skilled in the art in various embodiments to fulfill at least in part some, but not necessarily all of the previously identified needs.

BRIEF DESCRIPTION OF THE DRAWINGS

The teachings of the present invention can be readily understood by considering the following detailed description in conjunction with the accompanying drawings, in which:

FIG. 10 is a schematic elevational view of a camera head articulation and rotation (pan) mechanism of the optical camera inspection system of FIG. 5, showing the Φ and θ degrees of motion;

FIG. 11 is a schematic plan view of a camera head articulation and rotation (pan) mechanism of FIG. 10;

To facilitate understanding, identical reference numerals have been used, where possible, to designate identical elements that are common to the figures.

DETAILED DESCRIPTION

After considering the following description, those skilled in the art will clearly realize that the teachings of the present invention can be readily utilized in optical camera systems for nondestructive internal inspection of power generation machinery, including by way of non-limiting example steam or gas turbines and generators. Images can be obtained while the power generating machine rotor is rotating up to 1000 RPM. In some embodiments, internal components of gas and steam turbines are inspected with an optical camera inspection system that is capable of automatically or manually positioning the camera field of view (FOV) to an area of interest within the turbine along a pre-designated navigation path and capturing images with or without human intervention. In some embodiments, camera positioning and image capture can be initiated automatically or after receipt of operator permission. In other embodiments the camera can be manually positioned under human control, such as with a joy stick or other human machine interface device. The inspection system includes an articulated multi-axis inspection scope with an optical camera that can be advantageously inserted through a combustor nozzle access port, combustor and transition, so that the camera FOV captures the leading edge of Row 1 rotating turbine blades while the rotor is spinning at up to 1000 RPM. An illumination system strobe light and the camera image capture are synchronized with the blade rotation speed so that images of multiple or all blades may be obtained from a single inspection scope insertion point. Camera resolution and image acquisition speed are chosen to avoid blurry images of the rotating blades, such as through use of an exemplary so-called "full frame" or "global shutter" camera that captures images of all camera pixels substantially simultaneously.

In some embodiments, the optical camera inspection system is capable of automatically positioning the camera field of view (FOV) to an area of interest within the machinery and capturing images without human intervention. Automatic camera positioning and image capture can be initiated automatically or after receipt of operator permission. Alternatively, the system may be human-operated in "manual" mode.

Camera Inspection System Overview

Figure 1:
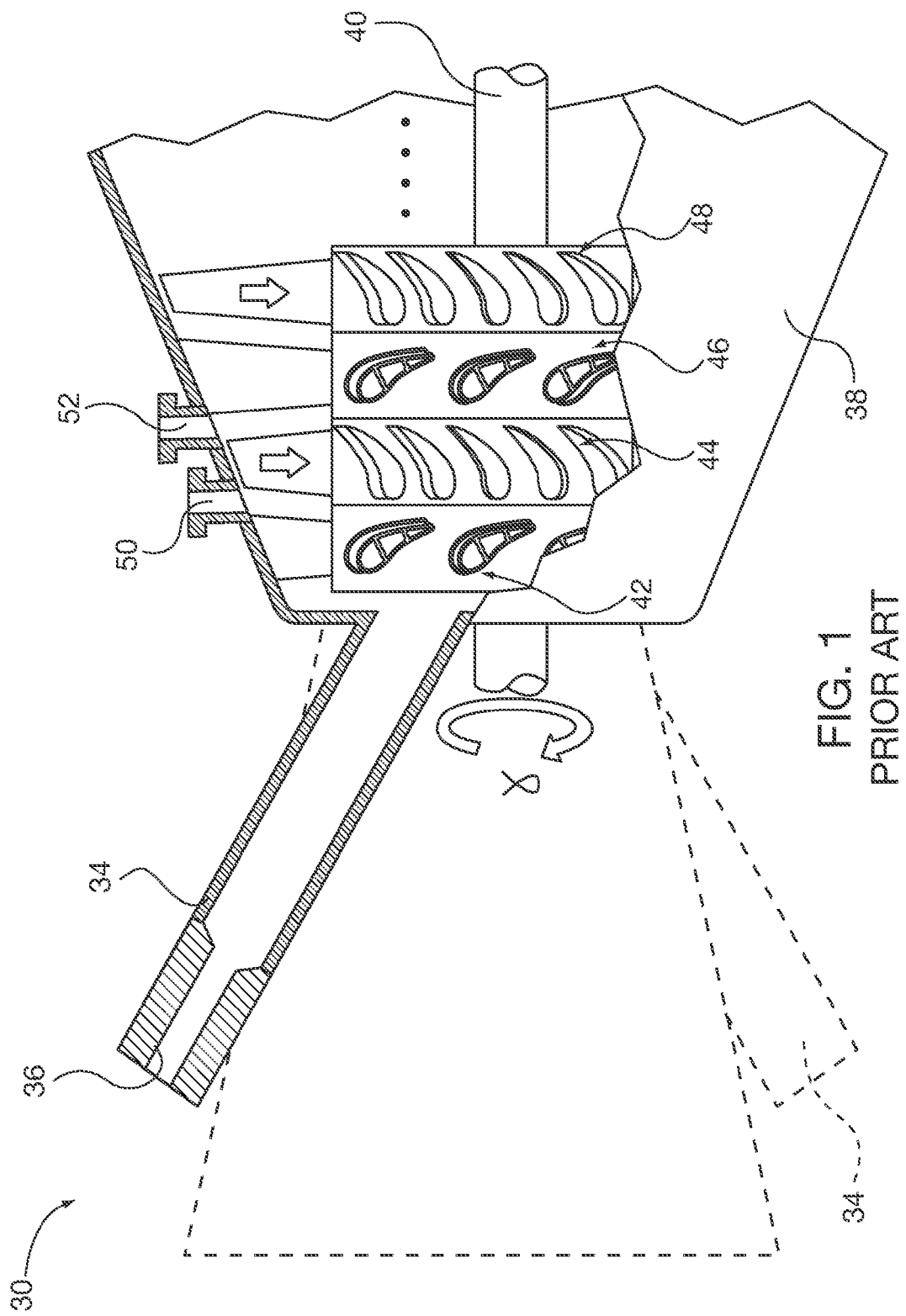
FIG. 1 is a partial cross sectional schematic view of a known gas turbine.
Figure 3:
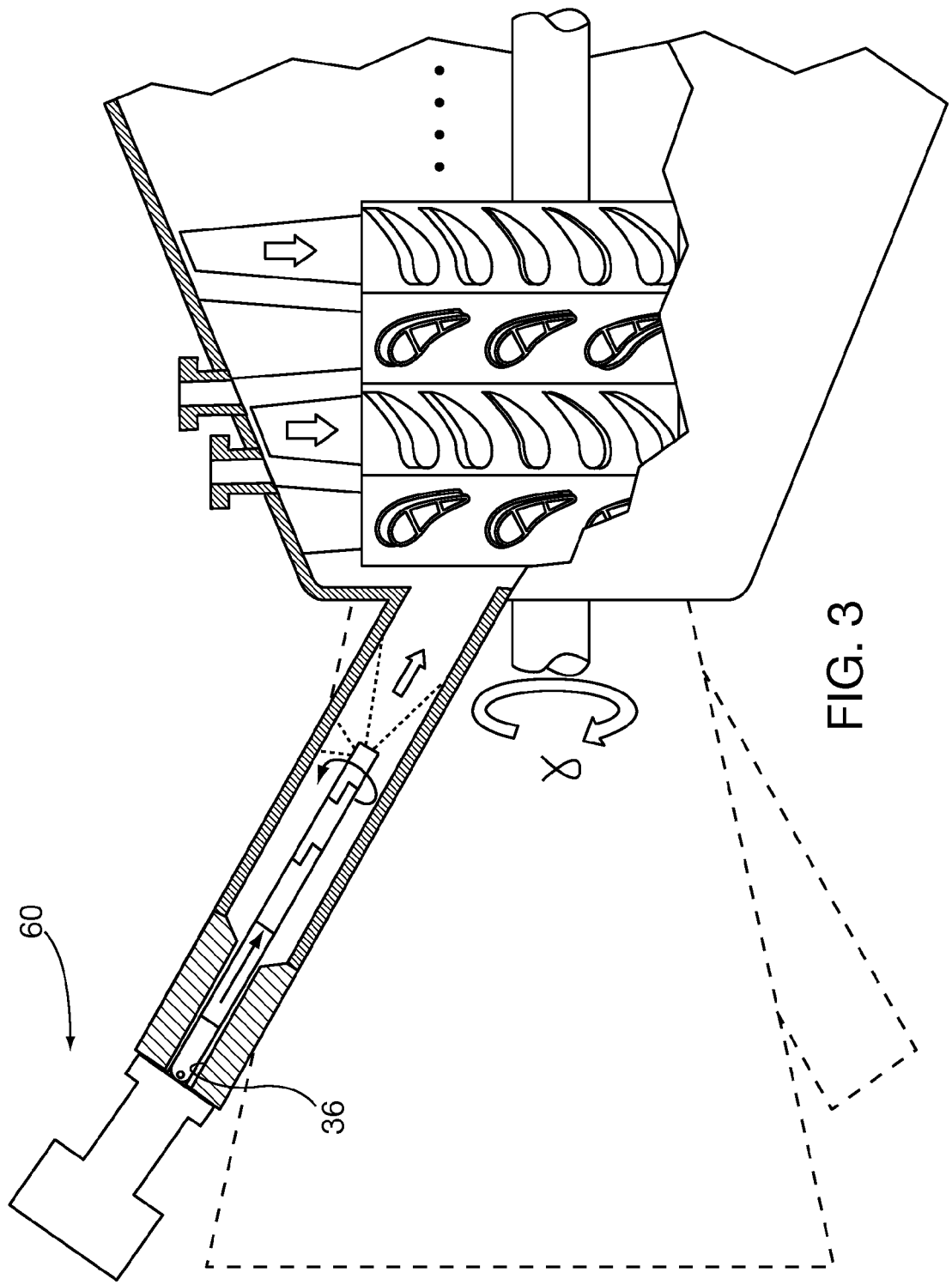
FIG. 3 is partial cross sectional schematic view of a known gas turbine performing an inspection of a combustor internal components with the optical camera inspection system of FIG. 2.
Figure 4:
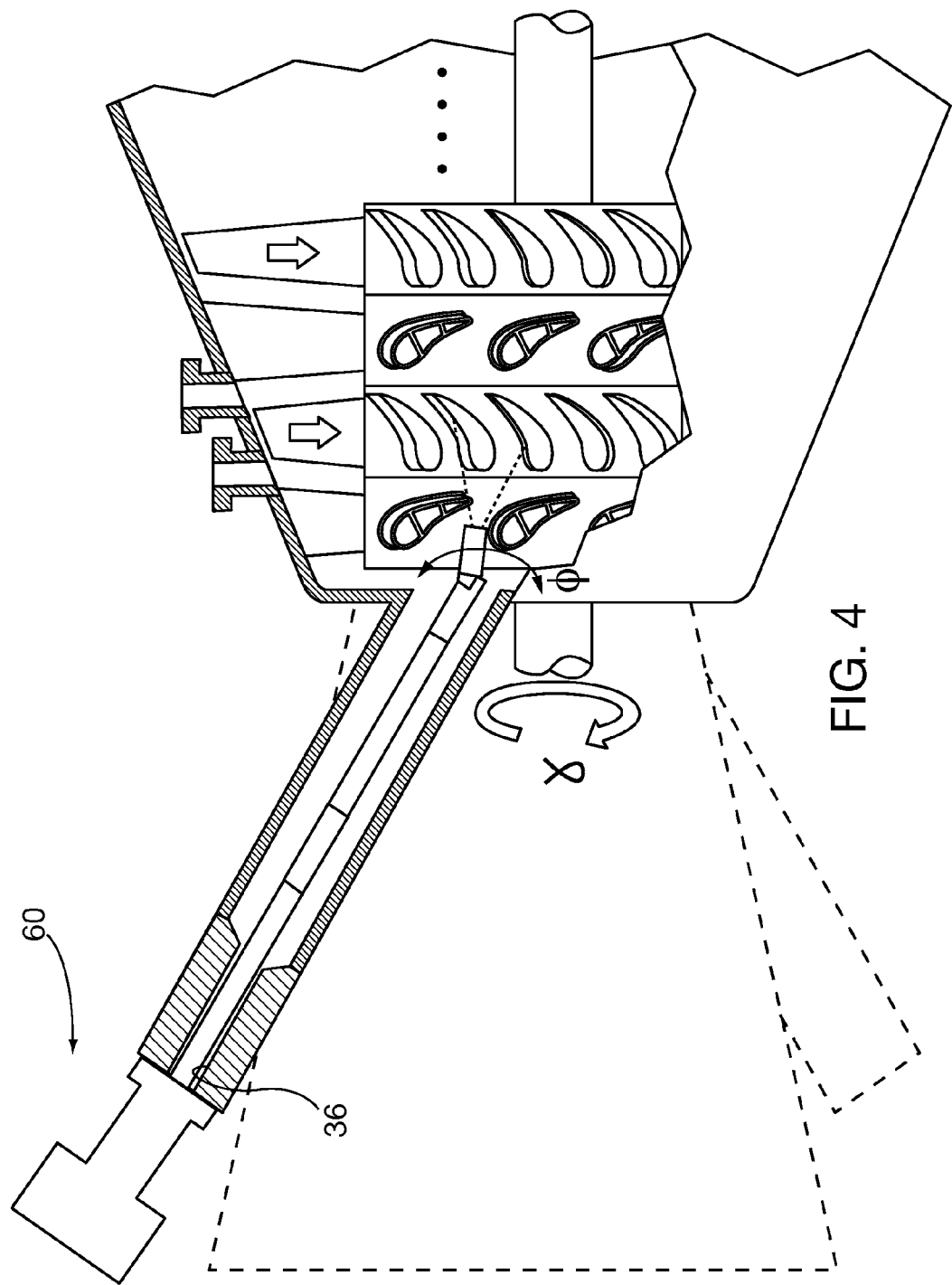
FIG. 4 is partial cross sectional schematic view of a known gas turbine performing an inspection of the leading edge of row 1 turbine blades with the optical camera inspection system of the present invention.
Figure 18:
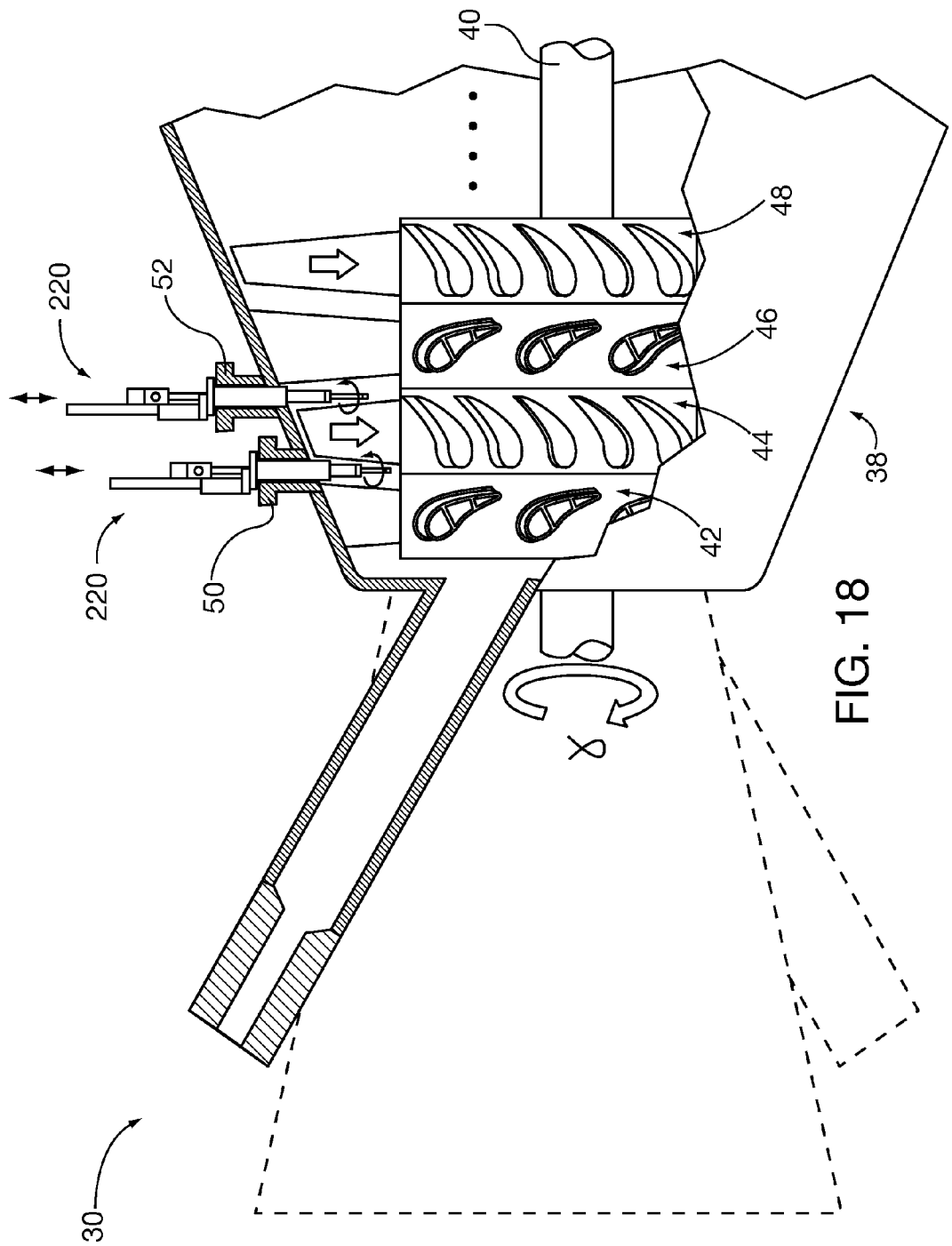
FIG. 18 is a partial cross sectional schematic view of a known gas turbine showing insertion of another optical camera inspection system embodiment that is described in the present specification into two separate turbine section rows respective inspection ports.

Referring to FIGS. 1, 4 and 18, embodiments of the camera inspection system described in this specification facilitate automated off-line remote visual inspection of gas turbine 30 internal components, including combustion section combustors and transitions 34, turbine section Row 1 and Row 2 fixed vanes 42, 46; leading Row 1 and Row 2 rotating blades 44, 48; and ring segments. As shown in FIGS. 2-4 and 18, inspection system embodiments described herein enable inspection of offline turbines that have not fully cooled to ambient temperature by attaching remote-actuated optical camera inspection scope probes 60 or 220 to turbine inspection ports such as a combustor nozzle port 36, or other ports 50 and 52 within the gas turbine 30 turbine section. Upon attachment, the inspection scope probes 60 or 220 are selectively positioned (manually in some embodiments by an operator or automatically in other embodiments without an operator) via internal motion control servo motors that are under command of a motion control system. Image data are acquired, captured, and if desired archived for further analysis.

Articulated Inspection Scope

Figure 2:
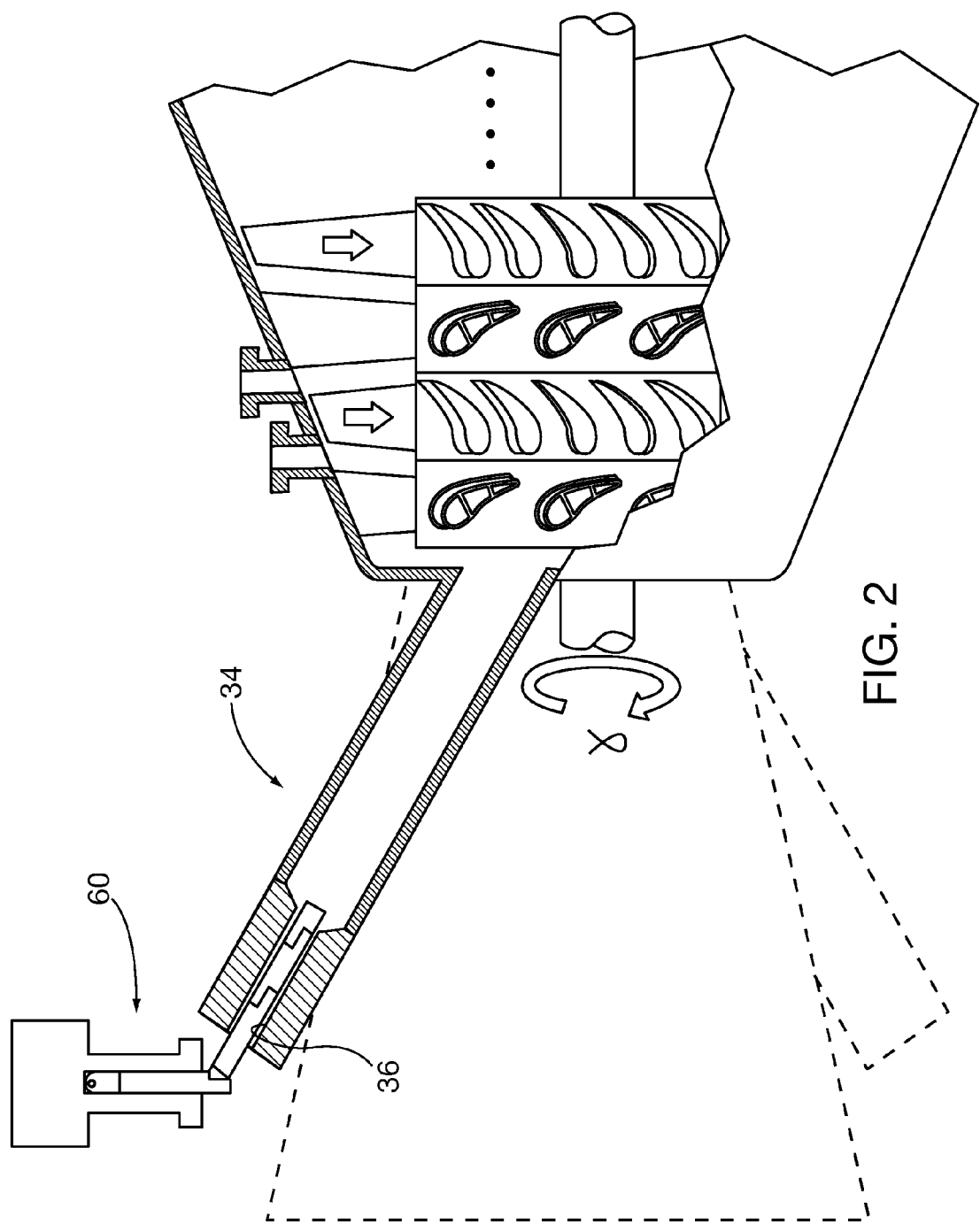
FIG. 2 is a partial cross sectional schematic view of a known gas turbine showing partial insertion of an optical camera inspection system embodiment described in this specification into a combustor inspection port.

FIGS. 2-4 show inspection of an off-line gas turbine by insertion (FIG. 2) of one of two alternative embodiments of an articulated inspection scope 60 into a combustor nozzle port 36, which functions as an inspection port. For maneuvering clearance of the scope 60 about the confines of a gas turbine installation, inspection scope 60 has a folding knuckle, so that the scope can be folded into a generally L-shape profile about half as long as an elongated scope. Once the 60 is positioned within the inspection port 36, the knuckle is straightened, as shown in FIG. 3. After the inspection scope 60 is affixed to the inspection port 36 it may be utilized to inspect to combustor and transition internal components by rotating and extending its camera head. In the scope embodiment of FIG. 4, as the scope 60 is further extended and its camera head articulated images of the Row 1 vanes and leading edge of Row 1 blades may be acquired. If the turbine rotor is in turning mode, images of all Row 1 blades may be captured as they rotate past the camera head field of view, as will be discussed in greater detail herein with reference to FIGS. 21-23.

Figure 5:
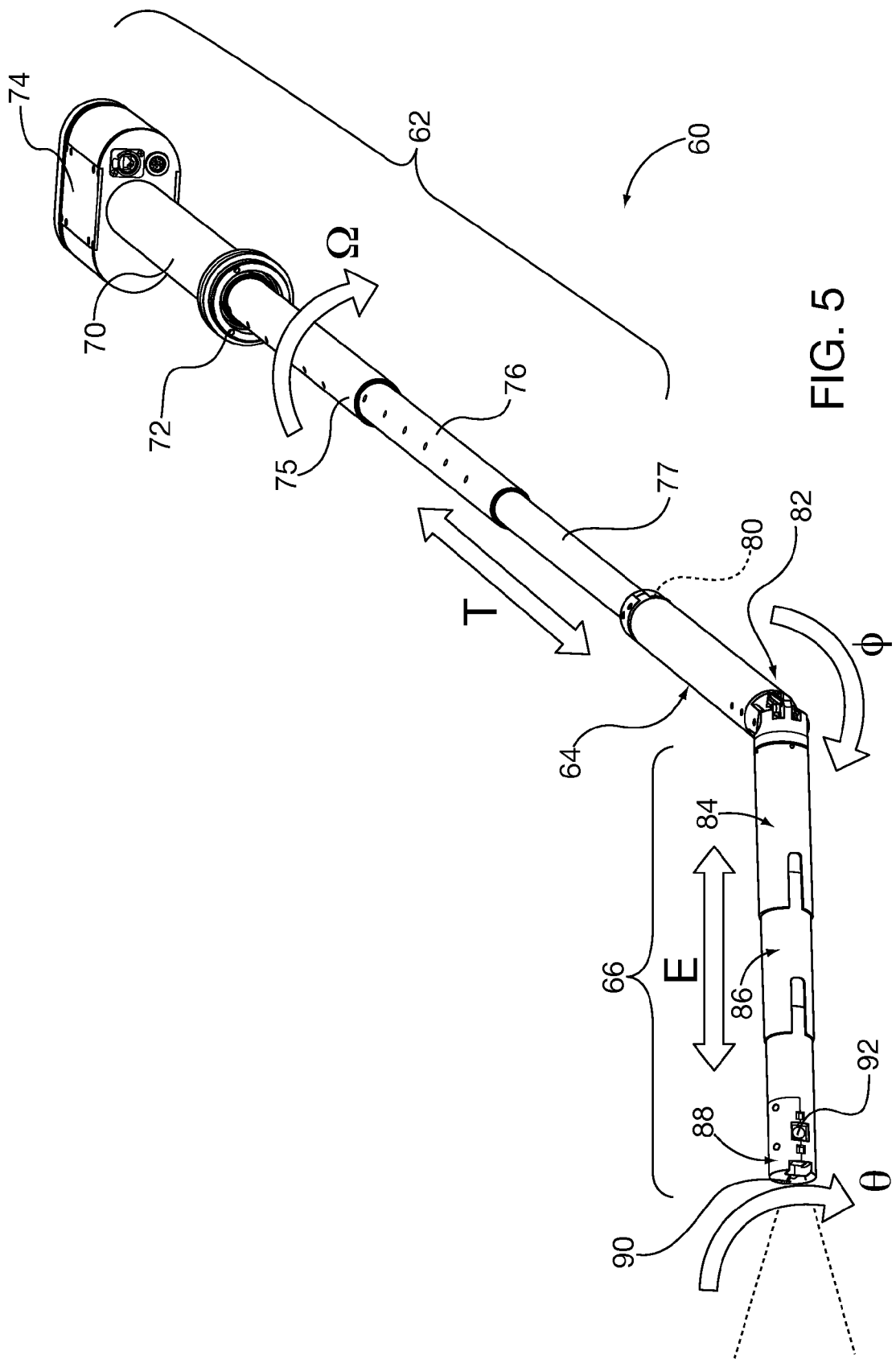
FIG. 5 is a perspective schematic view of the optical camera inspection system of the embodiment of FIG. 2, showing available degrees of motion $\Omega$, T, $\Phi$, E and $\theta$.

Referring to FIG. 5, the inspection scope 60 embodiment shown therein has three main component sections: extension tube section 62 (see FIGS. 5-9); motor can 64 (FIGS. 5, 10-12); and camera tip 66 or head (FIGS. 5, 12-15 and 21-22) that are capable of performing the following five degrees of motion freedom:

Ω—gross rotation;
T—telescoping extension;
Φ—camera head articulation;
E—camera head tip extension; and
θ—Camera head rotate/pan.

The extension tube section 52 has a mounting tube 70 and mounting collar 72 that are attached to an inspection port, such as the combustor inspection port 36. Motor housing 74 is attached to the opposite end of mounting tube 70 distal the mounting collar 72 and houses the servo motors necessary to perform the Ω and T degrees of motion. Three telescoping tubes 75-77 collapse into the mounting tube 70 for providing the T directional motion.

Figure 6:
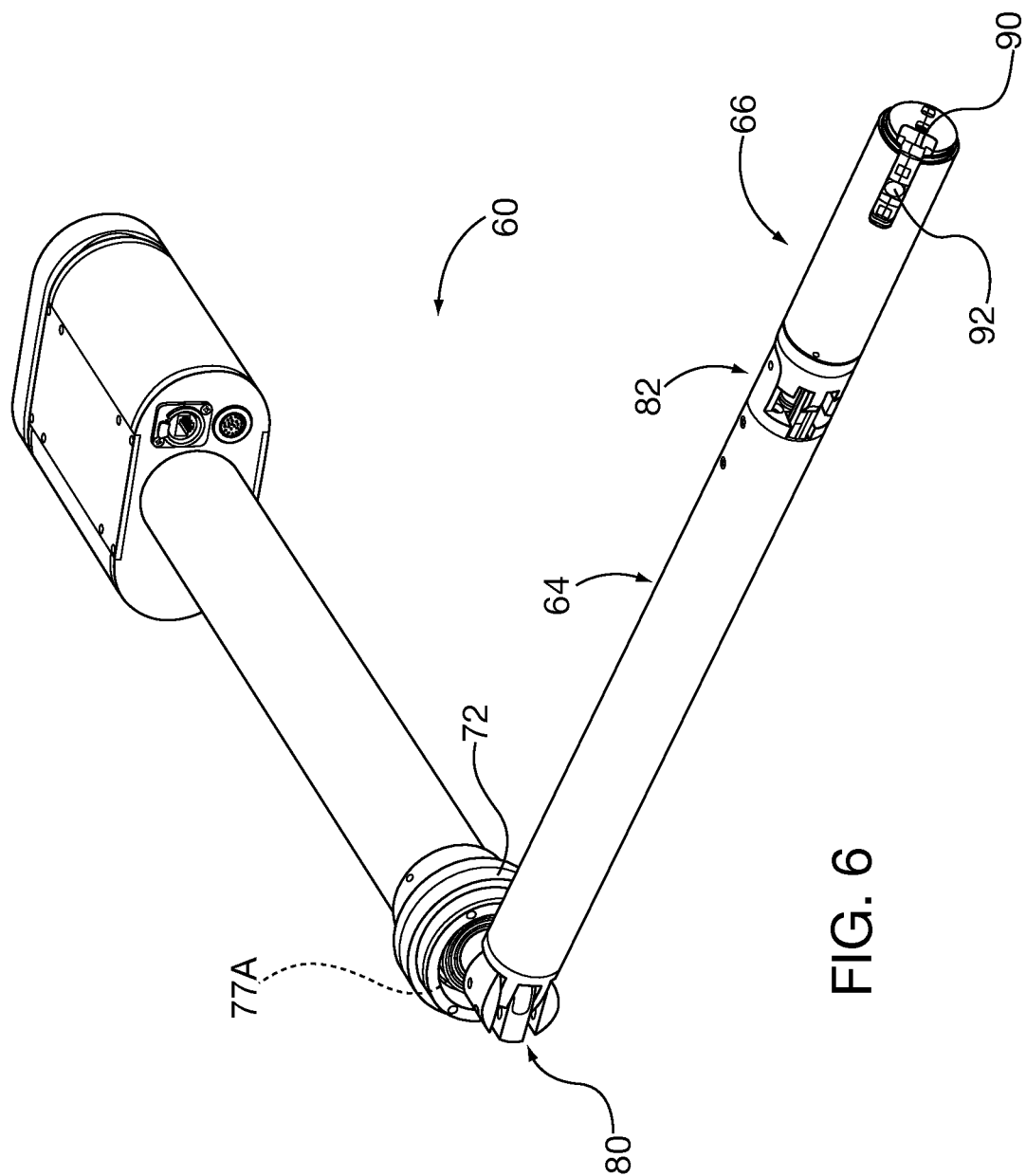
FIG. 6 is a perspective schematic view of the optical camera inspection system of FIG. 5, in the folded insertion position of FIG. 2.
Figure 7:
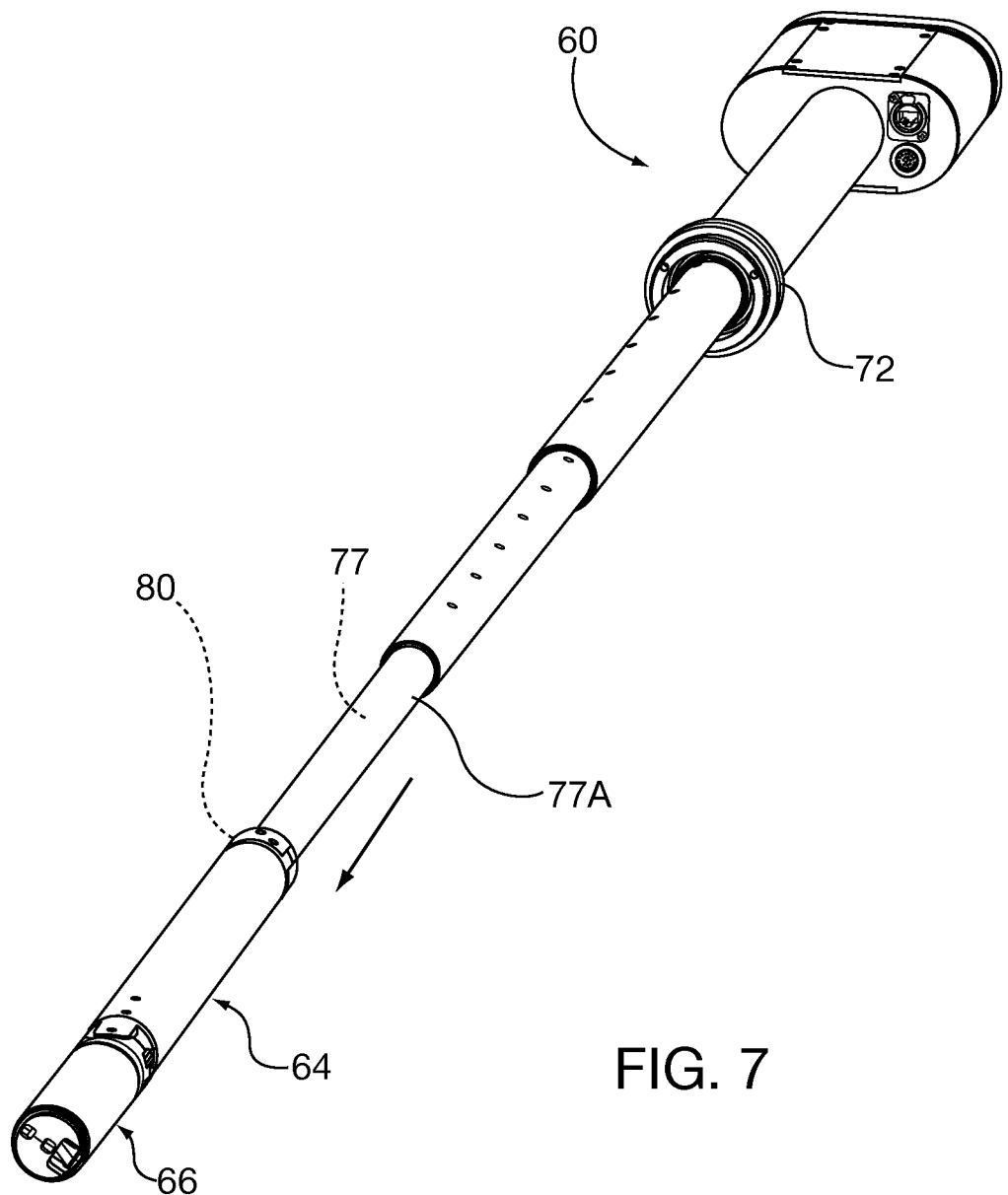
FIG. 7 is a perspective schematic view of the optical camera inspection system of FIG. 5, in the locked inspection position of FIG. 3.

As shown in FIGS. 6 and 7, spring loaded locking knuckle 80 enables the entire inspection scope 60 to fold for compact maneuvering about the turbine 30, as shown in FIG. 2 and described above. Locking sleeve 77A slides over telescoping tube 77 and restrains knuckle 80 therein when the inspection scope 60 is in is locked inspection position as shown in FIG. 7.

As shown in FIG. 5, motor can 64 houses the servo motors necessary to position motorized articulating joint 82 that provides the Φ degree of motion, the camera head 66 head extension motion E via the camera head telescoping extensions 84, 86 and the camera head 88 rotate/pan degree of motion θ. The camera head 88 includes camera ports 90, 92 for respective axial and lateral fields of view (FOV).

Figure 8:
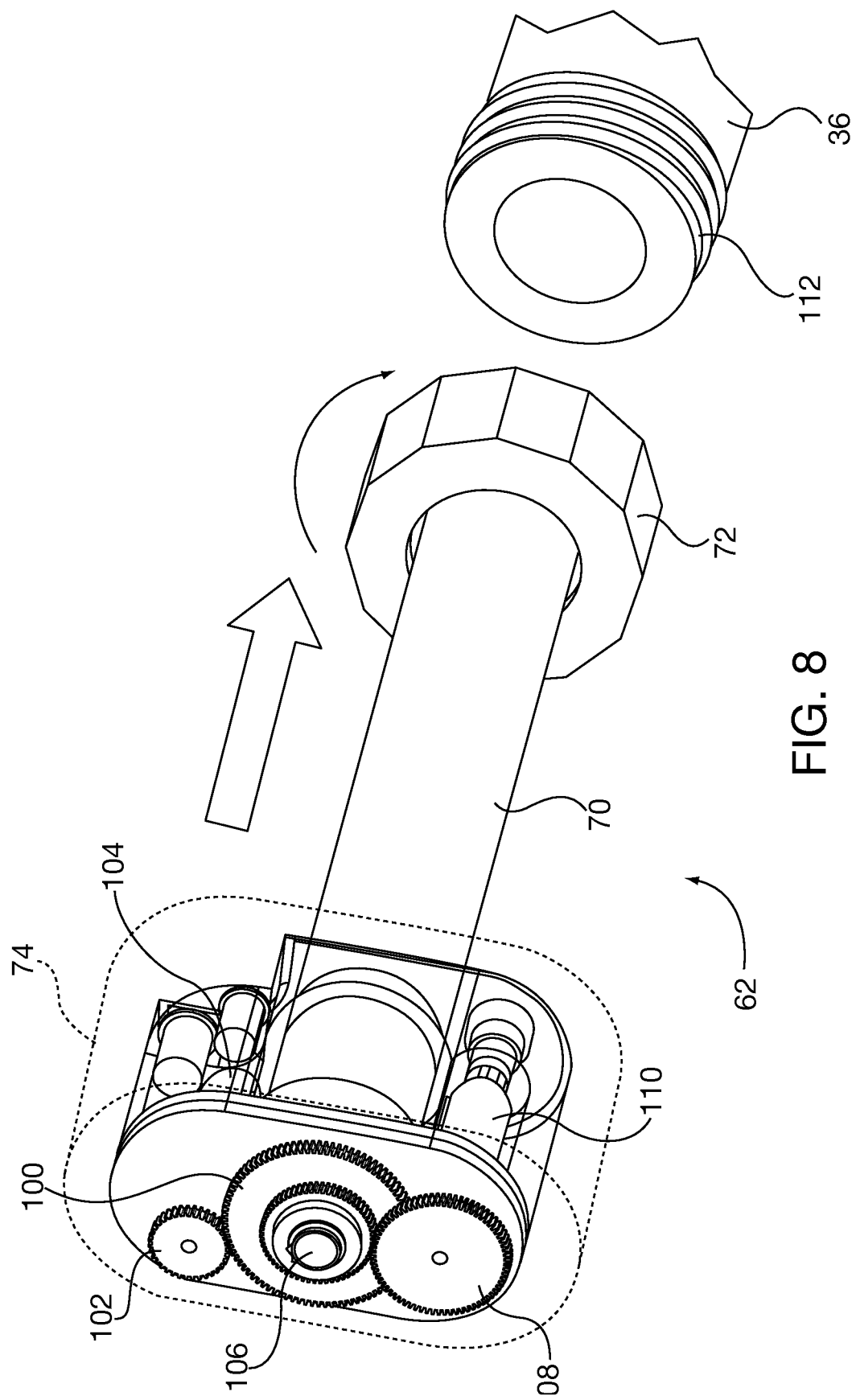
FIG. 8 is a perspective schematic view of the extension tube mechanism portion of the optical camera inspection system of FIG. 5, showing the Ω and T degrees of motion.
Figure 9:
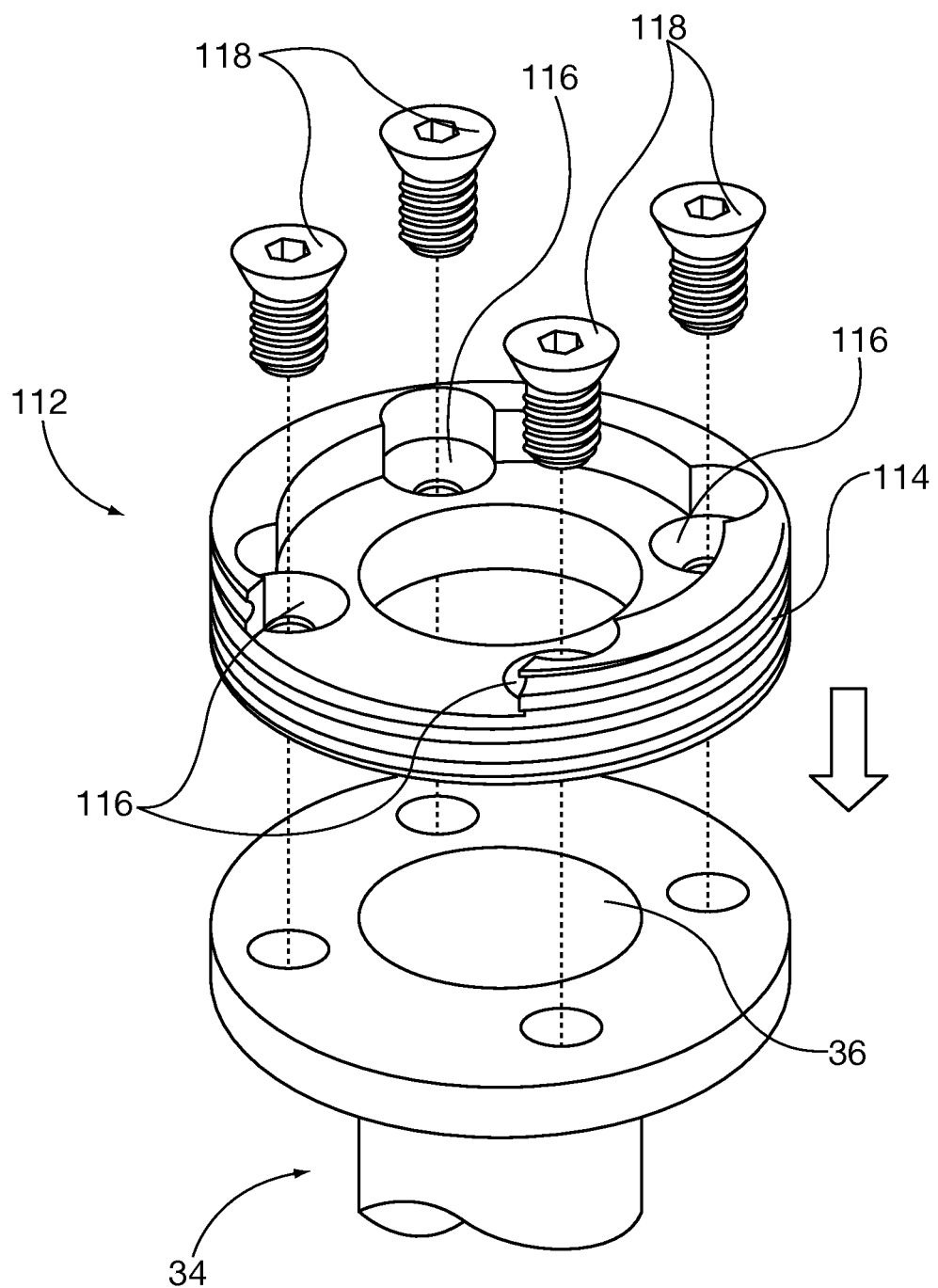
FIG. 9 is a schematic perspective view of an adapter ring of the present invention being attached to a turbine inspection port.
Figure 12:
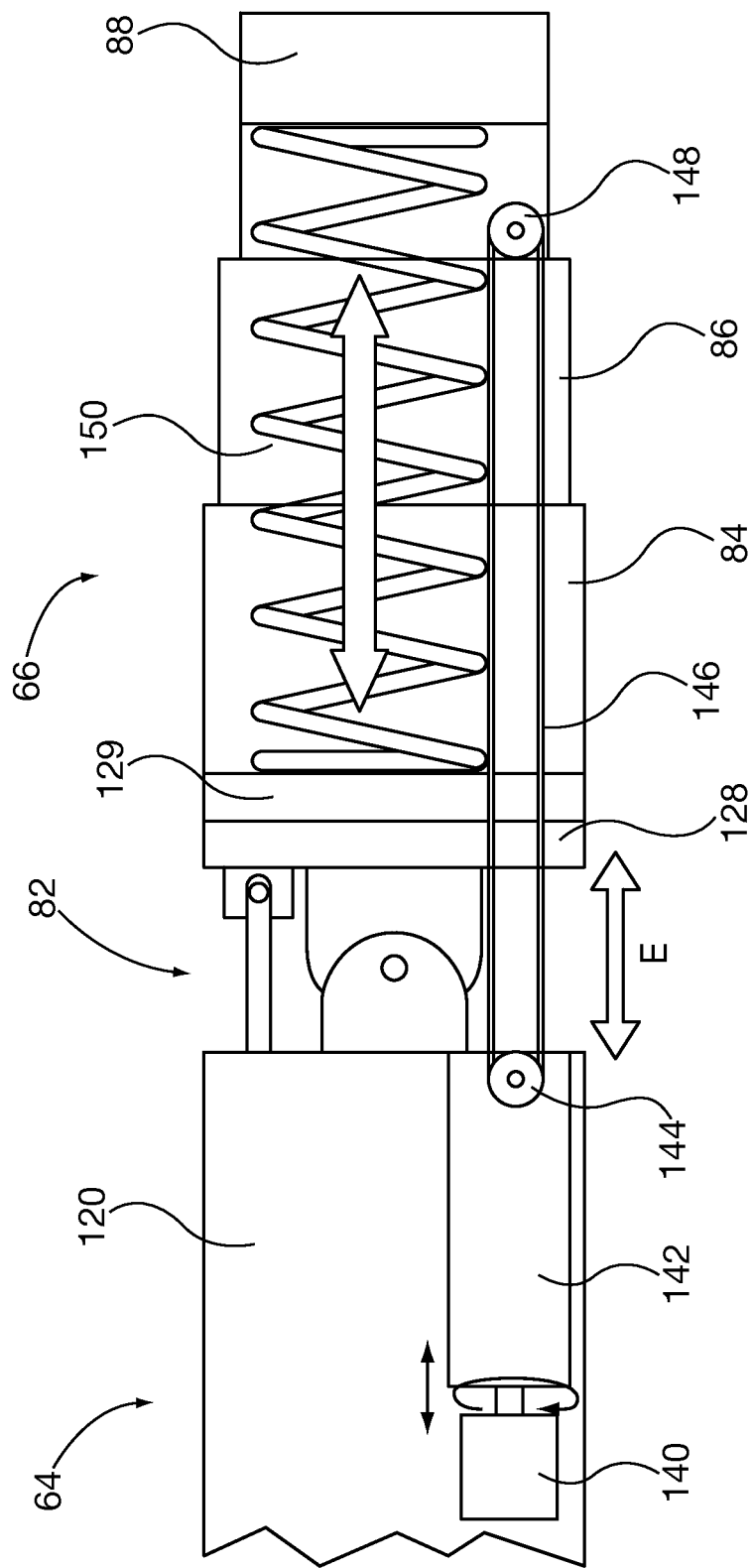
FIG. 12 is a schematic elevational view of a camera head extension mechanism of the optical camera inspection system of FIG. 5, showing the E degree of motion.

FIG. 8 is a detailed view of the motor housing 74, showing two coaxially nested, independently driven large and small diameter gears in the rotation hub 100. Rotate drive gear 102 is driven by the rotate servo motor 104, for effectuating the Ω motion by rotating the larger diameter gear in the rotation hub 100. Telescope extension drive screw 106 is rigidly coupled to the smaller diameter gear in rotation hub 100, that in turn engages the extend drive gear 108. Extend servo motor 110 is responsible for effectuating the T motion by rotating the smaller diameter in the rotating hub 100. Mounting collar 72 attaches to adapter ring 112, that is in turn attached to an inspection port, such as the combustor nozzle inspection port 36. As shown in FIG. 9, the adapter ring includes a plurality of peripheral threads 114 that are engaged with mating internal threads within the collar 72. The adapter ring 112 has mounting holes 116 for receipt of tapered head machine screws 118. The screws 118 may be captively mounted within adapter ring 112. Other configurations of adapter ring or other forms of base that affixes the scope to an inspection port may be substituted for the adapter ring 112.

Referring to FIG. 10, motor can 64 has a motor can housing 120 with a pair of spaced apart ear-like motor can pivots 122. Articulate motion servo motor 124 rotates drive screw 126 that imparts the Φ articulating motion by tipping camera pivoting hub 128. The tipping motion axis 132 is established between camera hub pivot 130 that is rotatively coupled to the motor can pivot 122. Offset link 133 is coupled to drive screw 126 and converts linear motion to rotational motion about tipping motion axis 132.

Motor can housing 120 also contains camera pan/rotate servo motor 134 that imparts the θ degree of motion on camera head 66, as shown in FIG. 11. Servo motor 134 drives bevel gear train 136, which in turn includes the driven bevel gear that is rotatively captured within camera pivoting hub 128, for in turn rotating the rotating hub 129. The rotating hub 129 is rigidly coupled to the camera head telescoping extension 84. Camera tip telescoping extensions 84 and 86 are extended and retracted in the E motion degree by extension servo motor 140 that in turn engages linear drive screw 142. The drive screw 142 includes drive pulley 144, over which passes tensioned cable 146. Slave pulley 148 is attached to camera head 88 and is also coupled to cable 146. Coil spring 150 is interposed between camera head 88 and rotating hub 129, and biases them away from each other, thereby tensioning cable 146. It follows that selective translation of the drive screw 142 by the extension servo motor 140 moves the camera head 88 to the left and right in the figure (motion E).

Figure 13:
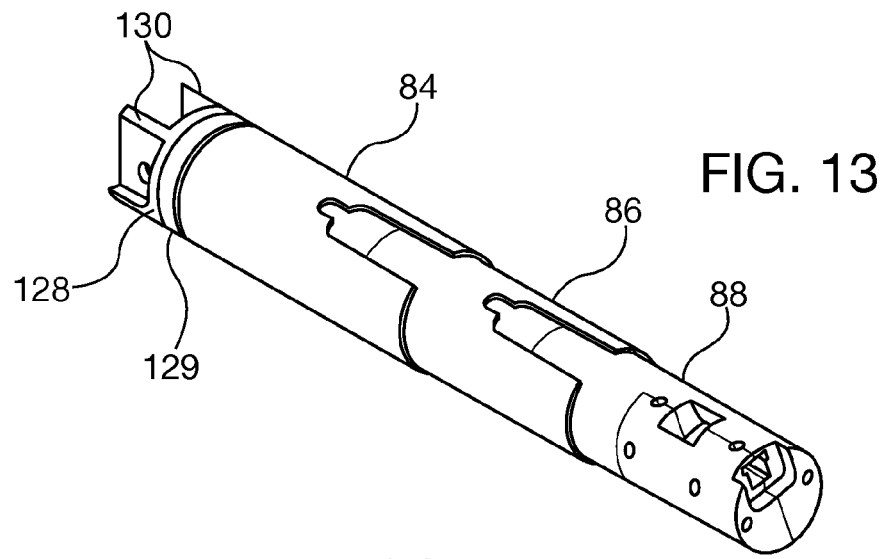
FIG. 13 is a schematic perspective view of the camera head of the optical camera inspection system of FIG. 5.
Figure 14:
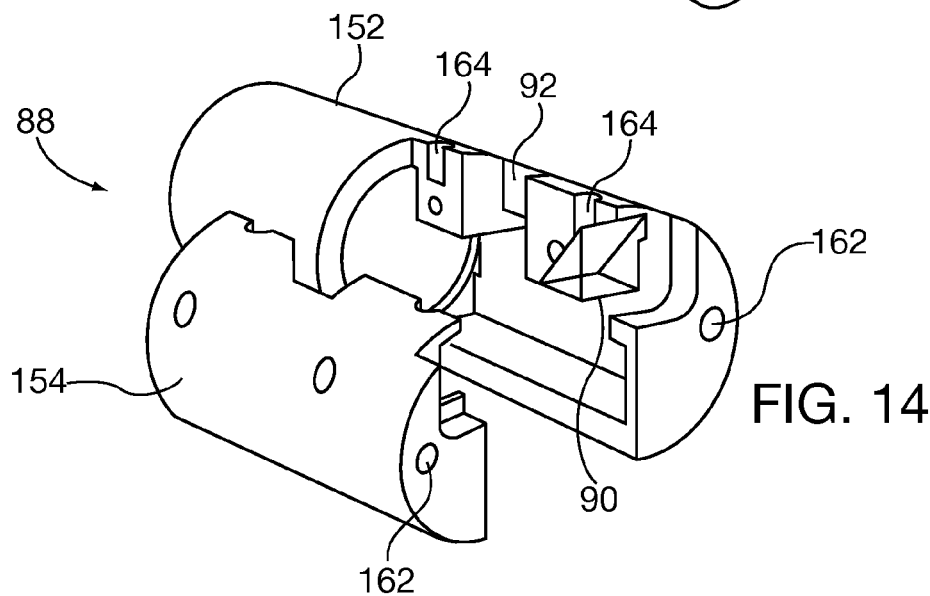
FIG. 14 is a schematic exploded perspective view of a camera head of the optical camera inspection system of FIG. 5.
Figure 15:
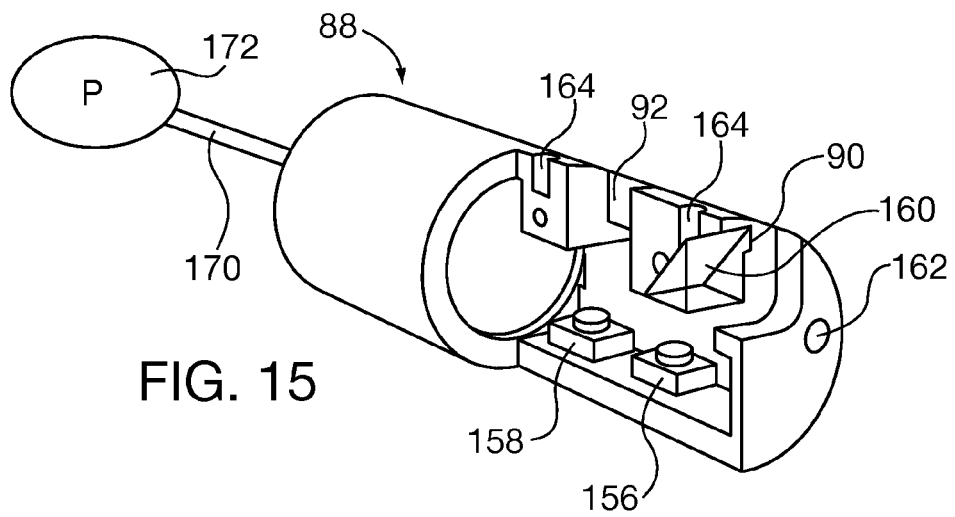
FIG. 15 is a schematic partial assembly perspective view of the camera head of FIG. 14.

FIGS. 13-15 show a camera head 88 embodiment that has a clamshell construction with camera head housing 152 and selectively removable cover 154. Camera 156 has a field of view (FOV) through "camera 1" port 90, extending along the central axis of the camera head 88. Camera 158 has a field of view (FOV) through "camera 2" port 92, extending laterally or normal to the central axis of the camera head 88. Camera 156 generates its image through prism 160. Cameras 156, 158 are known auto-focusing USB cameras of the type routinely used with personal computers. Light emitting diodes (LEDs) 162 and 164 provide illumination for the cameras 156, 158 during internal inspection of power generation machinery. One or two cameras having different resolution and focus properties may be substituted for auto-focusing USB cameras. Similarly the camera head illumination system may employ LEDs or other illumination sources of desired output intensity or other characteristics, including by way of non-limiting example: (i) steady-state or pulsed strobe illumination; or (ii) variable or dimmable intensity outputs.

Figure 21:
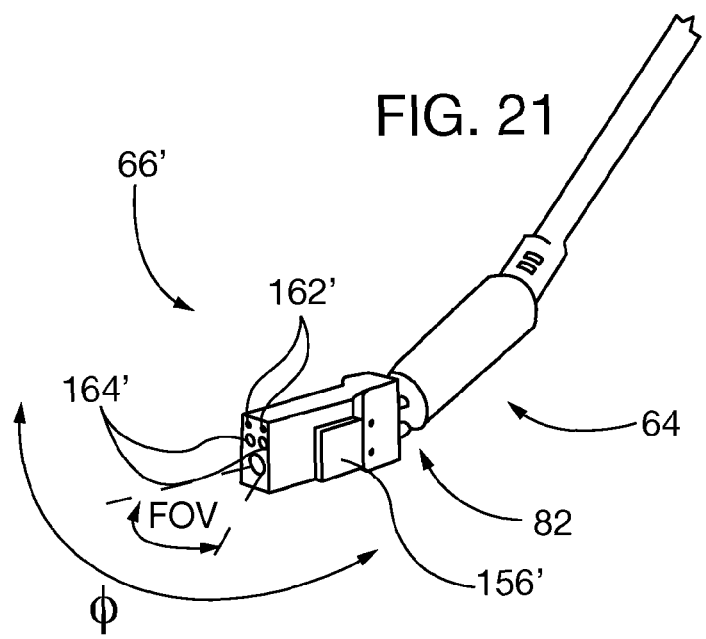
FIG. 21 is a perspective view of an optical camera inspection system embodiment of the present invention with a camera head capable of capturing images of Row 1 turbine blades while the turbine is in turning gear mode.
Figure 22:
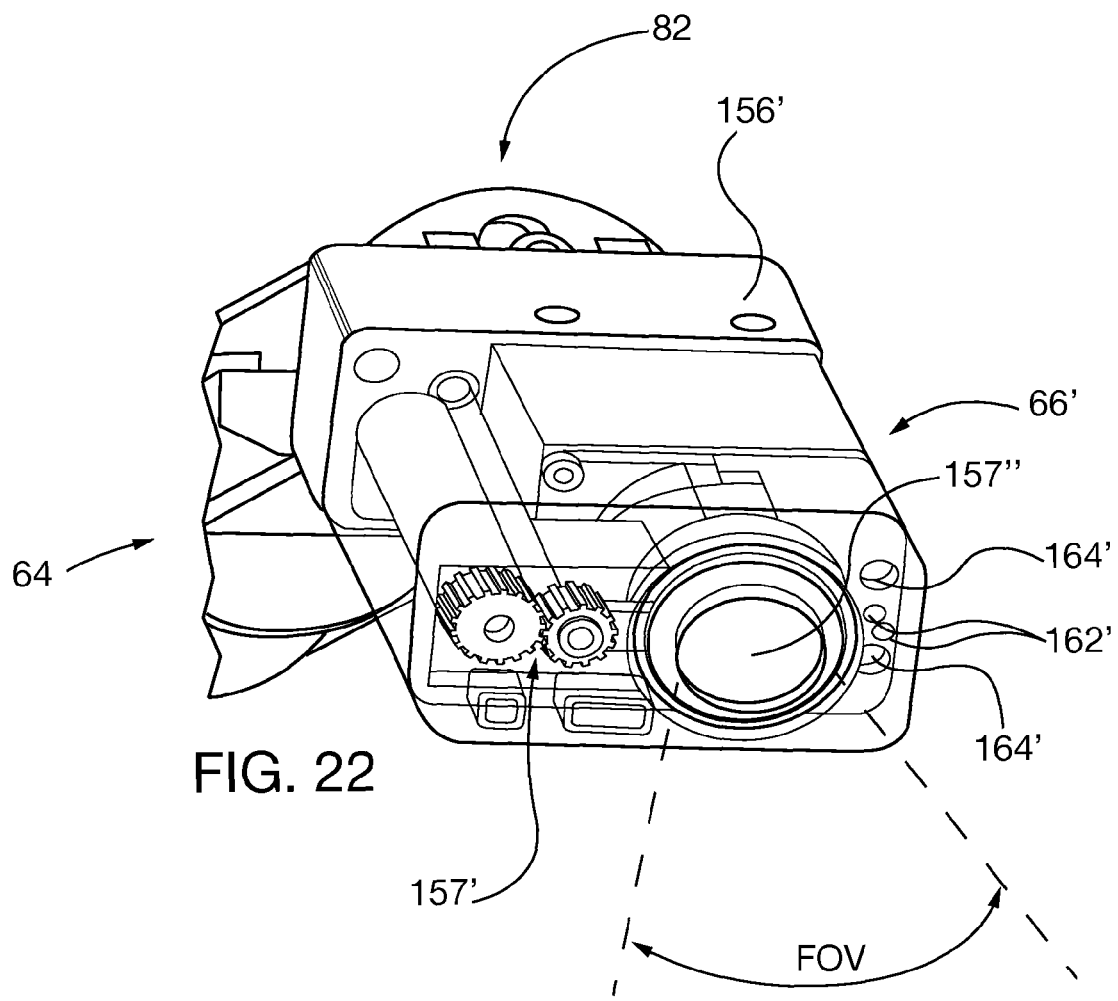
FIG. 22 is a perspective view of the camera head of the camera inspection system embodiment of FIG. 21.

An alternative embodiment camera tip or head 66' is shown in FIGS. 21 and 22 that substitutes for the tip or head 66 described in prior figures. Camera head 66' is coupled to the camera pivoting hub 128, which forms the distal end of articulation joint 82. The remainder of the previously described inspection scope system tube section 62 and motor can 64 components including the articulation joint 82 are utilized with the alternative embodiment camera head 66'.

Camera 156' is preferably a "full frame", also referred to as a "global shutter" camera that captures images of all camera pixels simultaneously or virtually simultaneously. The camera 156' preferably has a resolution of 2 mega pixels or greater, and a frame rate sufficiently high to capture individual images of rotating Row 1 rotor blades while the rotor is rotating at up to 1000 RPM without image blurring. A suitable camera is a Genie family camera available from Teledyne DALSA, Billerica, Mass., USA. The camera 156' includes a zoom focus drive 157' that may be automatically or manually adjusted for magnification. Preferably the inspection system 60 has no optical hardware, such as fiber optic pipes or viewing windows between camera objective lens 157" and the object of interest within the FOV, in order to capture more light photons with less likelihood of rotating blade captured image blurring. The camera 156' field of view (FOV) is oriented parallel to the camera head 66' central axis. Alternatively the FOV can be reoriented to any desired position relative to the camera head 66' central axis, for example by utilizing a prism or preferably by physically reorienting the camera and its objective lens 157". While a single camera is shown in FIGS. 21 and 22 multiple cameras may be mounted in the camera head 66' as is shown in the camera head 66 of FIGS. 13-15.

The inspection scope 60 embodiment of FIGS. 21 and 22 has an illumination system shown comprising pairs of LED lights 162' and 164' that are mounted co-axial with the camera head 66' central axis to illuminate the camera 156' FOV during scope insertion within the turbine and/or during an inspection procedure. The LED lights 162' and 164' may be oriented in any desired position, including transverse to the camera head 66' central axis, as shown in FIGS. 13-15.

Inspection scope 60, utilizing either of the camera head embodiments 66 or 66', is preferably externally cooled by a cooling air line 170 and pressurized cooling air source 172 (e.g., compressed air), schematically shown in FIG. 15. Cooling air passes through the scope 60 to transfer heat away from the instrument, where it exhausts through gaps within the scope outer surface, such as the camera ports 90, 92, the prism 160, around the cameras 156, 158 and the LEDs 162, 164. Those gaps effectively function as cooling air exhaust ports. Cooling air exhausting the various cooling ports helps transfer heat out of the scope 60 and helps create a thermal barrier around the camera head 88 that is relatively cooler than the not fully cooled turbine 30 internal temperature. In this manner the inspection scope 60 can be inserted into still hot shut-down turbine many hours before it cools to ambient air temperature. In this manner inspection can be initiated many hours—and possibly days—earlier than was permissible with known inspection systems. In this manner an inspection process can be initiated and completed earlier in a turbine service period than was possible in the past, possibly reducing the aggregate maintenance cycle time.

Camera Inspection Scope Control and Operation

Figure 16:
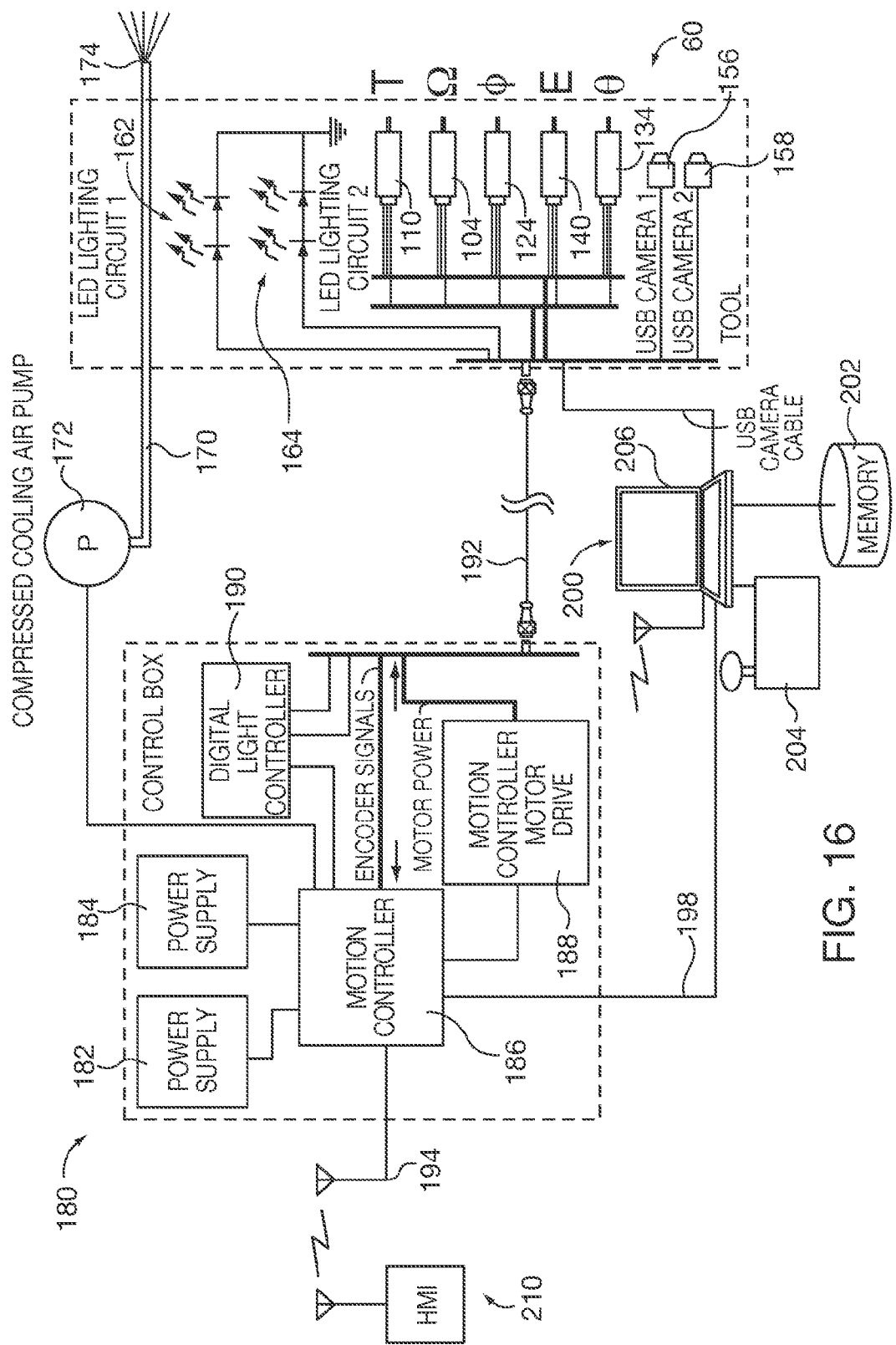
FIG. 16 is a block diagram of the control box and controls system for the optical camera inspection system of FIG. 5.
Figure 23:
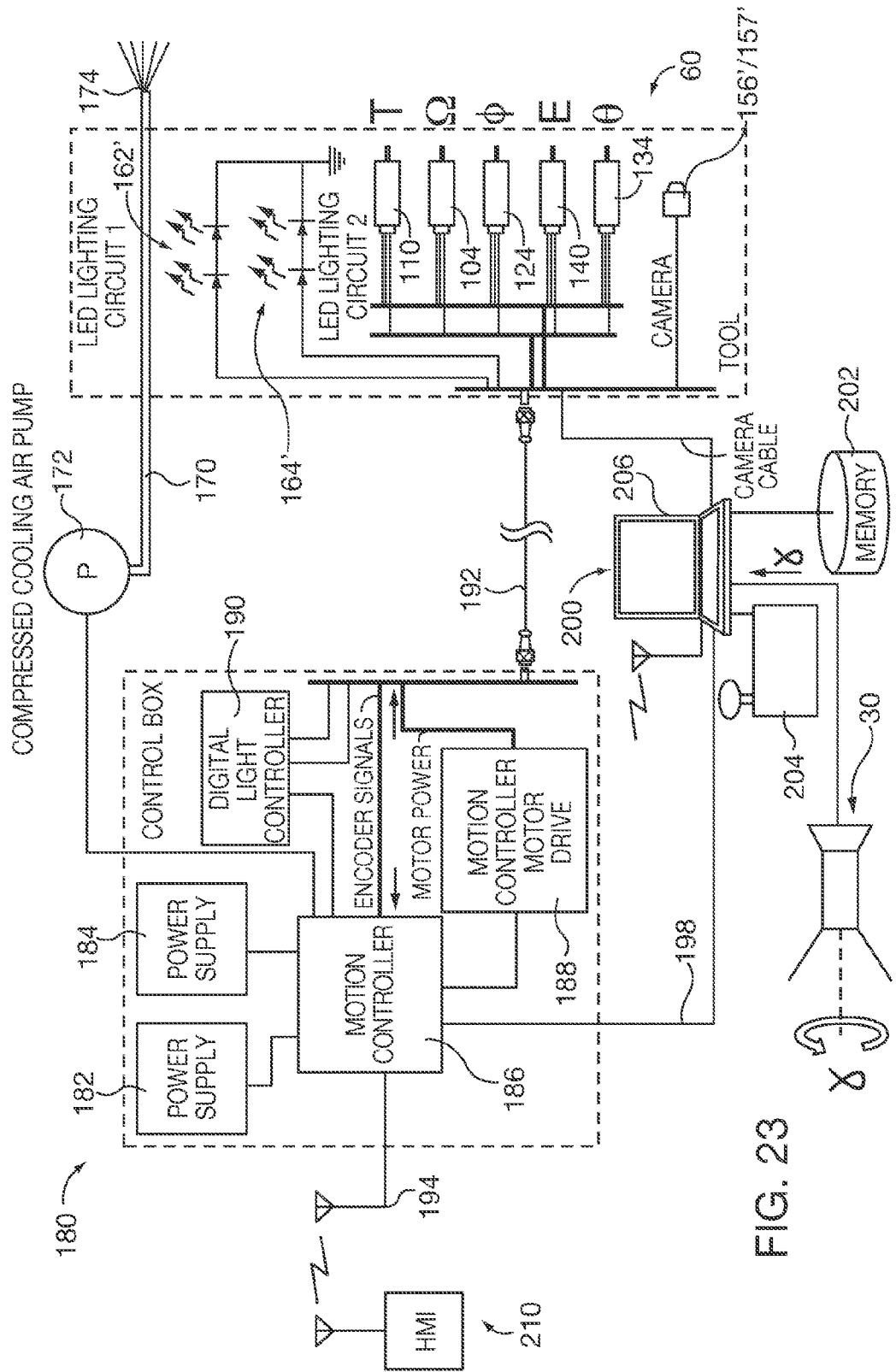
FIG. 23 is a block diagram of the control box and controls system for the optical camera inspection system of FIG. 21.

Inspection scope 60 positioning along its five degrees of motion are accomplished by energizing the five previously described precision motion control servo motors 104 ($\Omega$), 110 (T), 124 ($\theta$), 124 ($\Phi$), and 140 (E). The servo motors have associated encoders that provide motor position information feedback for use by the controller of a known motion control system. FIG. 16 is block diagram of an exemplary motion control system that is utilized with the camera head 66 of FIGS. 13-15. A corresponding block diagram for the camera head 66' of FIGS. 21 and 22 is shown in FIG. 23. In both FIGS. 16 and 23 common components and function are indicated with identical number and include the following common operational description. The previously described inspection scope 60 hardware is designated by dashed line 60, and is in communication with control box 180, also designated by dashed line, by way of known communication pathways, such as multi-pathway cable 192 and respective camera cables.

In either of the embodiments of FIGS. 16 and 23 control box 180 includes first and second power supplies 182, 184 for powering motion controller 186 and motion controller motor drive 188. All of components 182-188 are of known design utilized for industrial motion control systems. The motion controller 186 issues commands to the motion controller motor drive 188 for energizing and reversing the inspection scope 60 servo motors 104 ($\Omega$), 110 (T), 124 ($\theta$), 124 ($\Phi$), and 140 (E). For brevity all such motors are collectively referred to as "servo motors". The respective servo motors have associated encoders that generate encoder signals indicative of the scope position within its respective range of motion. For example, the encoder associated with servo motor 104 generates a rotational position signal indicative of the gross rotational position ($\Omega$) of the extension tube portion 62. Position signal information from each encoder is accessed by the motion controller 186. The motion controller 186 correlates respective motor encoder signals with inspection scope 60 spatial position. Digital light controller 190 controls the LEDs 162, 164 or 162', 164', luminal output and on/off (including strobe function, where applicable), and communicates with the motion controller 186 and host controller 200.

The motion controller 186 also controls cooling air flow into and through the inspection scope 60, for example flow rate out the cooling port 174.

In the embodiments of FIGS. 16 and 23, motion controller 186 has an optional wireless communication capability 194. Hardwired data pathway 198, for example a cable transmitting communications signals in conformity with Ethernet protocol, is in communication with the host controller 200. An exemplary host controller 200 is a personal computer with internal memory capacity and if desired external memory 202. In the embodiments of FIGS. 16 and 23 the host controller computer 200 receives and processes image data from camera 156 (USB Camera 1), camera 158 (USB Camera 2) and camera 156'/camera focus 157' that may be processed. The host controller 200 also controls operation of the cameras.

With respect to the full frame or global shutter 156' camera, the host computer also receives turbine RPM rotational speed information $\gamma$ from the gas turbine 30 speed sensing system, so that camera image capture rate and the LED lights 162' or 164' are pulsed/strobed in coordination with the turbine rotational speed to image plural Row 1 turbine blades from a single inspection FOV without significant image blurring. Utilization of a strobe lighting sequence during rotating blade inspection, more advantageously with a full frame global shutter camera and optically unobstructed, direct view between the camera 156' objective lens 157' and the inspected object of interest within the FOV facilitates higher turbine RPM image capture (e.g., up to approximately 1000 RPM) than is possible without a strobe lighting sequence. The illumination system may also selectively illuminate the camera field of view by varying illumination intensity and duration independent of turbine rotor rotational speed. The host controller computer 200 may archive or otherwise store raw or processed image data in memory 202. Inspection scope 60 can be positioned under human command and control, such as via HMI joystick 204 and/or HMI viewing/touch screen 206. Images from the cameras 156, 156', and 158 can be viewed by HMI viewing screen 206.

Figure 17:
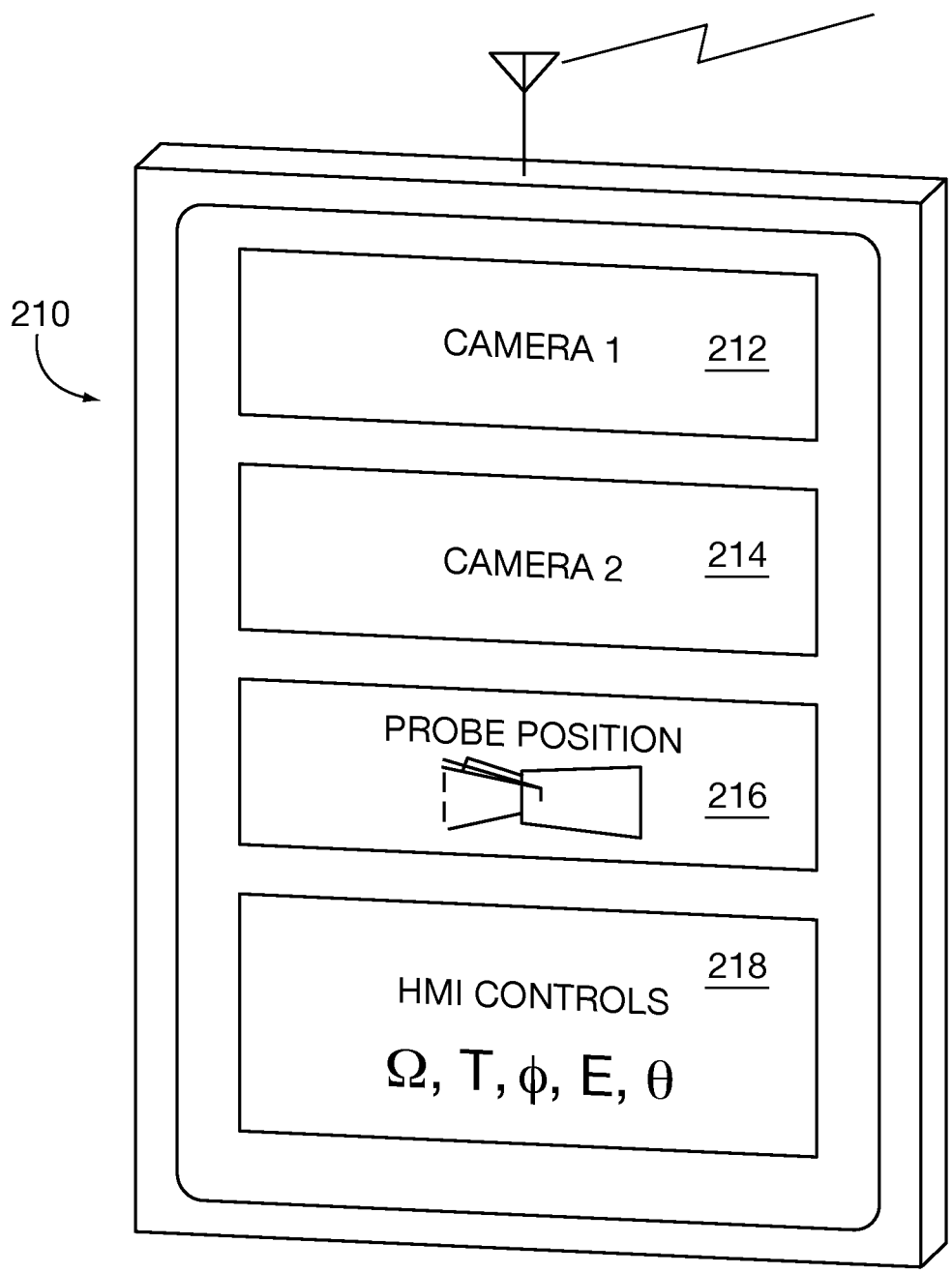
FIG. 17 is a perspective schematic view of an embodiment of a tablet computer human machine interface (HMI) for operator remote monitoring and control of the optical camera inspection system of the present invention.

Optionally the computer 200 may have wireless communication capability, for example to communicate with other computers, including for example a tablet computer 210 with HMI. FIG. 17 shows an exemplary tablet computer HMI display screen including Camera 1 image display 212, Camera 2 image display 214, probe position information display 216 and an HMI control interface 218 for manipulating inspection scope 60 positions. The tablet computer 210 may have direct communications capability with the motion controller 186, without the need to communicate through the host controller computer 200. The tablet computer HMI 210 may also be utilized with the inspection scope embodiment 60 shown in FIG. 23.

Blade/Vane Inspection Scope

Figure 19:
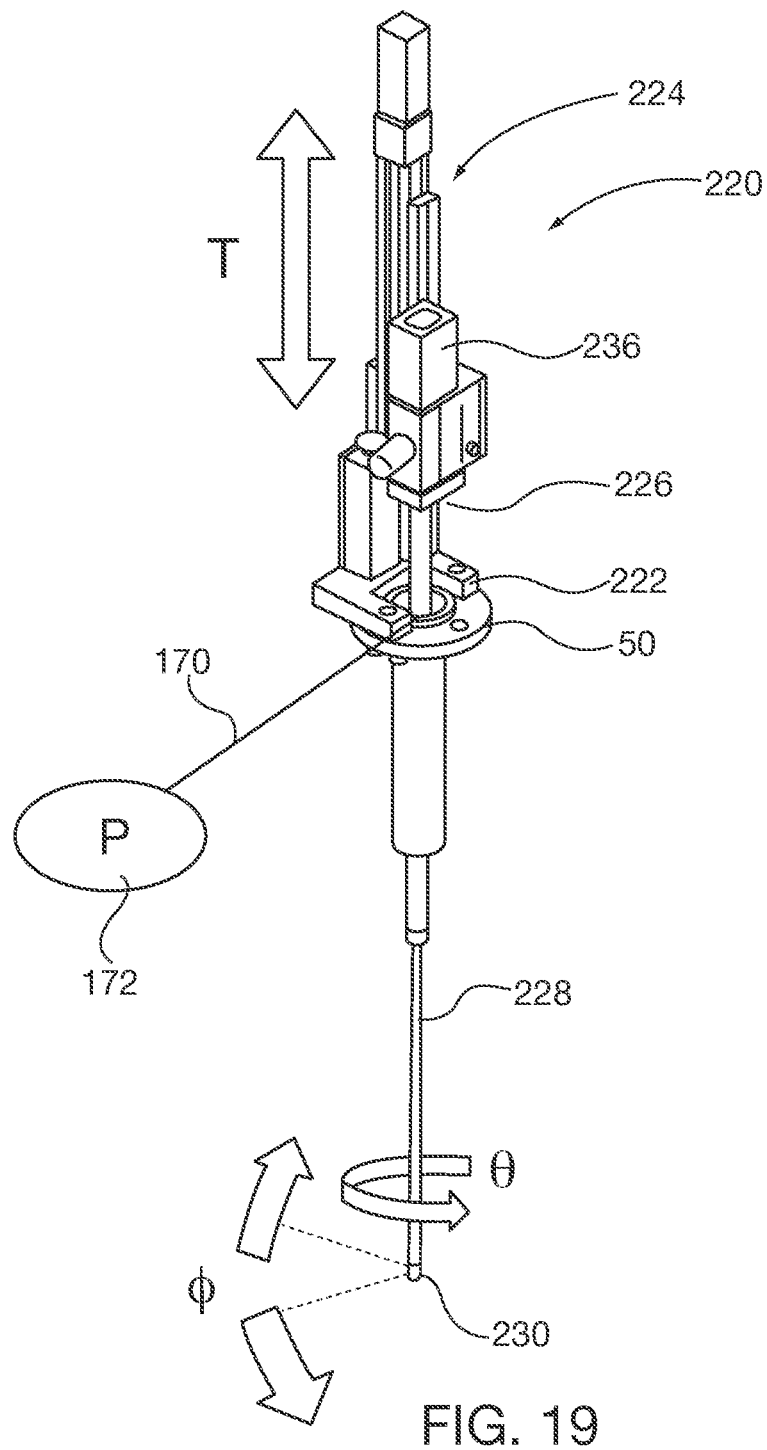
FIG. 19 is an elevational perspective view of optical camera inspection system embodiment of FIG. 18, showing available degrees of motion T, θ and Φ.
Figure 20:
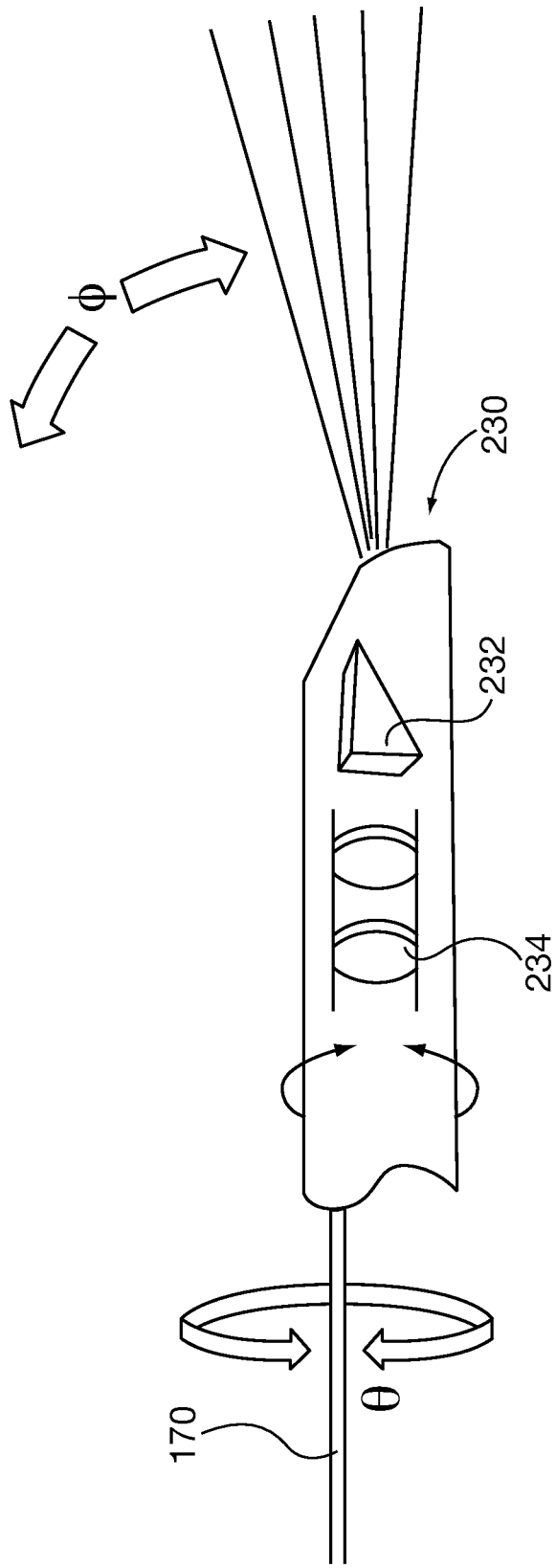
FIG. 20 is an elevational view of a swing prism articulation mechanism for the Φ degree of motion of the optical camera inspection system embodiment of FIG. 18.

A blade/vane inspection scope 220 embodiment is shown in FIGS. 18-20. This embodiment is particularly suitable for inspection within the confines of a gas turbine 30 turbine section 38, between rows of rotating blades and stationary vanes. FIG. 18 shows a pair of inspection scopes 220 respectively mounted to each of the Row 1 inspection port 50 and Row 2 inspection port 52. However, at the discretion of an inspection team a single inspection scope 220 may be mounted to a selected inspection port or more than two inspection scopes 220 may be mounted to the turbine 30 simultaneously during an inspection procedure. Similarly, an inspection team at its discretion may also operate one or more of the inspection scope 60 embodiments simultaneously with or without the inspection scope 220 embodiment in any inspection procedure.

As shown in FIGS. 19 and 20 the inspection scope 220 embodiment is mounted to a gas turbine inspection port (here a Row 1 inspection port 50) by mounting flange 222. Linear drive 224 with an associated servo motor and encoder translates the inspection scope in the telescoping extension position motion degree T. Rotational drive 226 with an associated servo motor and encoder rotates the inspection scope in the camera rotate/pan motion degree θ. Bore scope 228 is mechanically coupled to the linear drive 224 and rotational drive 226, and has a camera head 230 that captures within its field of view (FOV). The camera head 230 includes a pivoting prism 232 whose motion in the articulation Φ motion degree is imparted by an associated servo motor and encoder. The bore scope 228 is of known construction and includes fiber optic lenses 234 and auxiliary external lighting (not shown) that illuminate and transmit images within the camera head field of view to camera 236. The camera 236 may be an auto focusing USB camera that is coupled to a motion control system, such as shown in FIG. 16. General motion control and positioning of the inspection scope 220 along its motion degrees Φ, θ and T and camera image capture are performed as previously described with respect to the inspection scope embodiment 50.

The inspection scope 220 includes an external cooling system for inspection within a turbine 30 cool-down phase when the turbine section 30 still has an elevated temperature of up to approximately 150° C. As was described with respect to the inspection scope embodiment 50, the cooling system includes an air line 170 running in parallel to or within the bore scope 228 that expels cooling air obtained from a cooling air source through one or more functional cooling air exhaust ports, such as around the camera head 230.

The three motion degrees Φ, θ and T in the blade/vane inspection scope 220 embodiment are sufficient to obtain complete images of the leading or trailing sides of all rotating turbine blades within a given row while the turbine rotor is spinning in turning gear mode. For example in FIG. 18 the leading side of each of the Row 1 turbine blades 44 can be inspected by the inspection scope 220 that is positioned in inspection port 50. As each individual blade rotates within the camera head 230 field of view its image is captured by the associated control system. A partial or full series of blade images can be obtained during a single rotor 40 rotation while the turbine 30 is in turning gear mode. A single camera head 230 field of view may not capture the full radial length an area of interest on a turbine blade. By repositioning the camera head tilt angle Φ or inserting/retracting the bore scope 228 along the T freedom degree the camera field of view can be repositioned radially along the blade or vane length. Images captured at different blade/vane radial positions can be combined to create an aggregate image of the entire blade. Similarly, an image of the trailing edge of each blade 44 in Row 1 can be captured by positioning an inspection scope 220 in turbine inspection port 52, as was done for the leading edges.

Exemplary Turbine Inspection Procedures

Some camera inspection system embodiments described herein provide the capability of automatic positioning and image capture of an inspection camera field of view relative to an area of interest with a turbine, such as a gas turbine, without human intervention. After inspection scope positioning sequence information is provided to the system, subsequent inspections are repeatable by different inspection teams, regardless of their individual inspection scope positioning skill or inspection speed. Automated inspections can be completed quicker, with less likelihood of human-created errors, as compared to known inspection procedures. Further explanation of the inspection methods of the present invention will be with reference to inspection of an exemplary industrial gas turbine.

Automatic inspection scope positioning sequence information may be obtained by installing an inspection scope embodiment described herein on a selected inspection port and orienting all controlled motions to an initialized or "start" position. A human inspector guides the inspection scope through the control system HMI, e.g., by use of a joystick or touch screen pad, through a navigated path within the turbine that is recorded within one or both the control system controllers/host computer. The navigation path is chosen to orient the inspection scope camera head field of view within area of interest without causing undesirable impact of the scope with turbine internal components.

In automatic inspection scope positioning embodiments the control system retains the navigation path information from the initial human-controlled inspection and can subsequently repeat the inspection scope positioning sequence automatically for future inspection cycles on the same turbine or other turbines having the same internal structure. For example, a navigation path sequence can be performed on a single test turbine and the sequence can be communicated to other remote sites for use by inspection teams inspecting the same structure gas turbine located at that site. In the field, an inspection team may be concerned that a different gas turbine may have variations in internal structure from the original gas turbine. The field team may review the stored navigation path individual step by step, with local override to accommodate any path variations needed for the field installation turbine to perform an inspection, or may choose to program a new navigation path dedicated to the field location turbine.

Navigation paths alternatively can be determined in virtual space by a human inspector simulating a navigation path in a simulated turbine and recording the path for subsequent use in actual turbine inspections. As another alternative, a scope inspection simulation program can prepare a suggested inspection navigation path for review and approval by a human inspector.

A navigation path sequence can move the camera head field of view from one position of interest to another position of interest. For example, as shown in FIG. 4, an inspection scope can be affixed to a combustor nozzle port 36, whereupon the inspection system can capture and record images of internal components within the combustor and transition with assistance of steady-state lighting illumination from the illumination system, then move to the leading edge of Row 1 vanes to take their images. If Row 1 blade leading edge imagery is desired the inspection scope 60 camera head can pass between and extend through those vanes. Alternatively, when performing Row 1 blade leading edge imagery, the camera head can remain in the transition outside the leading edge of the Row 1 vanes, in which case the camera FOV is shifted by articulating articulation joint 82 along motion axis. This articulation shifting will allow the scope 60 to inspect the leading edge of Row 1 blades within the repositioned camera FOV and capture their images. If the turbine is in turning gear mode or otherwise rotating up to approximately 1000 RPM the camera head 66' embodiment, in conjunction with strobe illumination from the illumination system lights, can record sequentially the same image for each blade during a single rotor rotation.

When in a navigation path position the camera head embodiments 66 or 66' may be repositioned to obtain image information from different camera fields of view from the same reference point. The various images taken from the same reference point can be combined to obtain a composite or "stitched" view of the structural elements, or to take a virtual "tour" of any or all portions of the turbine interior.

Rather than move the inspection scope camera head field of view from one position to another, it is also possible to move the turbine component areas of interest within the field of view of a stationary camera head. For example, an inspection scope inserted between blade and vane rows or at the leading edge of the Row 1 blades can capture an image of each blade rotating within the camera field of view, whether the turbine is in turning gear mode or whether an operator manually "bumps" each blade of a completely stopped turbine rotor sequentially in front of the camera head.

Although various embodiments, which incorporate the teachings of the present invention, have been shown and described in detail herein, those skilled in the art can readily devise many other varied embodiments that still incorporate these teachings. For example, "optical images" of turbine internal component can be obtained in the visible light spectrum or in the infrared spectrum. The inspection scope motion degrees do not have to be limited to those exemplary motions enabled by the servo motors 104 (Ω), 110 (T), 124 (θ), 124 (Φ), and 140 (E). Scope motion does not have to be imparted by servo motors, and can include known alternative pneumatic or other motion control systems. Similarly, inspection system cameras, whatever their internal structure or operation, are chosen to facilitate capture of clear, non-blurred images of rotating turbine blades while the rotor is spinning at up to 1000 RPM.

What is claimed is:

1. A system for internal inspection of a turbine, comprising:
    a base for affixation to a turbine inspection port;
    an inspection scope having an extendable elongated body defining a central axis, with a proximal end rotatively coupled to the base and a distal end for insertion within a turbine inspection port; an extension portion intermediate the proximal and distal ends; and an articulation joint, having opposed first and second joint ends, with the first joint end coupled to the inspection scope distal end;
    a camera head, including a camera for capturing an image within a field of view, coupled to articulation joint second joint end;
    a gross rotation drive for rotating the inspection scope about its central axis, coupled thereto;
    a scope extension drive for translating the extension portion, coupled thereto;
    an articulation drive, for articulating the field of view relative to the inspection scope central axis, coupled to the camera head;
    an illumination system for selectively illuminating the camera field of view; and
    a control system, coupled to a turbine rotational speed sensing system, the gross rotation, scope extension and articulation drives, the camera and the illumination system, for positioning the inspection scope and field of view along a navigation path within a turbine to an internal area of interest, as well as for selectively illuminating the camera field of view with the illumination system in response to turbine rotor rotational speed information obtained from the speed sensing system, and capturing camera images at rates corresponding to said turbine rotor rotational speed information.

2. The system of claim 1, wherein the control system automatically and sequentially positions the field of view to plural areas of interest along the navigation path and captures respective images thereof.

3. The system of claim 1, the illumination system further capable of selectively illuminating the camera field of view by varying illumination intensity and duration independent of turbine rotor rotational speed.

4. The system of claim 1 wherein: the turbine is a gas turbine, the base is coupled to a combustor pilot nozzle port; the camera is a global shutter or full frame camera that captures all camera pixel images approximately simultaneously and the captured images are of Row 1 vanes or blades.

5. The system of claim 1, wherein the navigation path executed by the control system is determined by any one of:
    human controlled positioning of an inspection system within a turbine of the same type along a selected navigation path, and recording said navigation path for subsequent replication by the control system;
    human controlled simulated positioning of a virtual inspection system within a virtual turbine of the same type along a selected navigation path, and recording said navigation path for subsequent replication by the control system; or
    simulated positioning of a virtual inspection scope and virtual power generation machine of the same type along a simulated selected navigation path without human intervention, and recording said navigation path for subsequent replication by the control system.

6. The system of claim 1, further comprising:
    a first camera, capable of capturing images in a first field of view that is generally parallel with a central axis of the camera head; and
    a second camera, capable of capturing images in a second field of view that is generally laterally aligned with the camera head central axis.

7. A system for internal inspection of a gas turbine, comprising:
    a base for affixation to a gas turbine inspection port;
    an inspection scope having an extendable elongated body defining a central axis, with a proximal end rotatively coupled to the base and a distal end for insertion within a turbine inspection port; an extension portion intermediate the proximal and distal ends; and an articulation joint, having opposed first and second joint ends, with the first joint end coupled inspection scope distal end; a camera head extension coupled to the articulation joint second end and having a camera head telescoping portion; and a camera head rotation/pan joint also coupled to the articulation joint second end;
    a camera head, including a camera for capturing an image within a field of view, coupled to the camera head extension and the camera head rotation/pan joint;
    a gross rotation drive for rotating the inspection scope about its central axis, coupled thereto;
    a scope extension drive for translating the extension portion, coupled thereto;
    an articulation drive, for articulating the camera head field of view relative to the inspection scope central axis coupled to the camera head;
    a camera head extension drive for translating the camera head telescoping portion, coupled thereto;
    a camera head rotation/pan drive for rotating the camera head, coupled thereto;
    an illumination system for selectively illuminating the camera field of view; and a control system, coupled to the gross rotation, scope extension and articulation drives as well as the camera and illumination system, for positioning the inspection scope and field of view along a navigation path within a turbine to an internal area of interest, as well as for selectively illuminating the camera field of view with the illumination system and capturing camera images at rates corresponding to a turbine rotor rotational speed.

8. The system of claim 7, the illumination system further capable of selectively illuminating the camera field of view by varying illumination intensity and duration independent of turbine rotor rotational speed.

9. The system of claim 7, the control system further coupled to a turbine rotational speed sensing system and selectively illuminating illumination system in response to turbine rotor rotational speed information system obtained from the speed sensing system.

10. The system of claim 9, the illumination system further capable of selectively illuminating the camera field of view by varying illumination intensity and duration independent of turbine rotor rotational speed.

11. The system of claim 7 wherein: the turbine is a gas turbine, the base is coupled to a combustor pilot nozzle port, the camera is a global shutter or full frame camera that captures all camera pixel images approximately simultaneously and the captured images are of Row 1 vanes or blades.

12. The system of claim 11, further comprising:
a cooling system coupled to the inspection scope for routing pressurized cooling gas through the inspection scope and camera head;
the illumination system coupled to the camera head;
a first camera, capable of capturing images in a first field of view that is generally parallel with a central axis of the camera head; and
a second camera, capable of capturing images in a second field of view that is generally laterally aligned with the camera head central axis.

13. A method for internal inspection of a turbine, comprising the steps of:
providing an internal inspection system having:
a base for affixation to a turbine inspection port;
an inspection scope having an extendable elongated body defining a central axis, with a proximal end rotatively coupled to the base and a distal end for insertion within a turbine inspection port; an extension portion intermediate the proximal and distal ends; and an articulation joint, having opposed first and second joint ends, with the first joint end coupled to the inspection scope distal end;
a camera head, including a camera for capturing an image within a field of view, coupled to articulation joint second joint end;
a gross rotation drive for rotating the inspection scope about its central axis, coupled thereto;
a scope extension drive for translating the extension portion, coupled thereto;
an articulation drive, for articulating the camera head field of view relative to the inspection scope central axis coupled to the camera head;
a control system, coupled to the gross rotation, scope extension and articulation drives and the camera, for positioning the inspection scope and field of view along a navigation path within a turbine to an internal area of interest and for capturing a camera image thereof, and adapted for coupling to a turbine rotor rotational speed sensing system; and
an illumination system for selectively illuminating the camera field of view that is coupled to the control system;
rotating a turbine rotor at a rotational speed;
coupling the control system to a turbine rotor rotational speed sensing system of said turbine and obtaining rotor rotational speed information therefrom;
affixing the base to a turbine inspection port;
positioning the inspection scope and camera head field of view along the navigation path with the control system;
selectively illuminating the camera field of view with the illumination system at rates corresponding to the turbine rotor rotational speed information; and
capturing camera images at rates corresponding to the turbine rotor rotational speed information.

14. The method of claim 13, for capturing images of a gas turbine Row 1 vanes and Row 1 blades components, comprising:
coupling the base to a gas turbine combustor pilot nozzle port;
inserting the inspection scope through a gas turbine combustor pilot nozzle port;
illuminating the camera field of view while navigating the camera along a navigation path through the combustor and an adjoining combustor transition upstream of Row 1 blades and vanes components independent of turbine rotor rotational speed;
capturing a first camera image of at least one of the Row 1 vane components with the articulation joint in a first position;
selectively illuminating the camera field of view with the illumination system at rates corresponding to the turbine rotor rotational speed; and
articulating the articulation joint to a second position, and capturing respective second camera images of plural rotating Row 1 blade components with a camera that captures all camera pixel images approximately simultaneously.

15. The method of claim 13, wherein the navigation path executed by the control system is determined by any one of:
human controlled positioning of an inspection system within a turbine of the same type along a selected navigation path, and recording said navigation path for subsequent replication the control system;
human controlled simulated positioning of a virtual inspection system within a virtual turbine of the same type along a selected navigation path, and recording said navigation path for subsequent replication by the control system; and
simulated positioning of a virtual inspection scope and virtual power generation machine of the same type along a simulated selected navigation path without human intervention, and recording said navigation path for subsequent replication by the control system.

16. The method of claim 13, wherein during the inspecting step the control system automatically and sequentially:
selectively illuminates the illumination system;
positions the camera field of view to plural areas of interest along the navigation path by moving the inspection scope; and
captures respective images thereof with a camera that captures all camera pixel images approximately simultaneously.

17. The method of claim 13, the illumination system further capable of selectively illuminating the camera field of view by varying illumination intensity and duration independent of turbine rotor rotational speed.

18. The method of claim 17, for capturing images of a gas turbine Row 1 vanes and Row 1 blades components, comprising:
- providing a global shutter or full frame camera that captures all camera pixel images approximately simultaneously;
- coupling the base to a gas turbine combustor pilot nozzle port;
- inserting the inspection scope through a gas turbine combustor pilot nozzle port;
- illuminating the camera field of view while navigating the camera along a navigation path through the combustor and an adjoining combustor transition upstream of Row 1 blades and vanes components independent of turbine rotor rotational speed;
- capturing a first camera image of at least one of the Row 1 vane components with the articulation joint in a first position;
- selectively illuminating the camera field of view with the illumination system at rates corresponding to the turbine rotor rotational speed; and
- articulating the articulation joint to a second position, and capturing respective second camera images of plural rotating Row 1 blade components.

* * * * *